United States Patent [19]

Nappholz et al.

[11] Patent Number: 5,184,615
[45] Date of Patent: Feb. 9, 1993

[54] APPARATUS AND METHOD FOR DETECTING ABNORMAL CARDIAC RHYTHMS USING EVOKED POTENTIAL MEASUREMENTS IN AN ARRHYTHMIA CONTROL SYSTEM

[75] Inventors: Tibor A. Nappholz, Englewood; Albert K. Dawson, Denver; Richard M. T. Lu, Aurora; Bruce M. Steinhaus, Parker, all of Colo.

[73] Assignee: Telectronics Pacing Systems, Inc., Englewood, Colo.

[21] Appl. No.: 667,316

[22] Filed: Mar. 8, 1991

[51] Int. Cl.⁵ ............................................. A61N 1/368
[52] U.S. Cl. ........................ 128/419 PG; 128/419 D
[58] Field of Search ..................... 128/419 D, 419 PG

[56] References Cited

U.S. PATENT DOCUMENTS

| | | | |
|---|---|---|---|
| 3,587,398 | 12/1974 | Rubin | 128/419 D |
| 4,202,340 | 5/1980 | Langer et al. | 128/419 D |
| 4,291,699 | 9/1981 | Geddes et al. | 178/419 D |
| 4,393,877 | 7/1983 | Imran et al. | 128/419 D |
| 4,475,551 | 10/1984 | Langer et al. | 128/419 D |
| 4,692,719 | 9/1987 | Whigham | 332/11 D |
| 4,759,366 | 7/1988 | Callaghan | 128/419 PG |
| 4,766,900 | 8/1988 | Callaghan | 128/419 PG |
| 4,796,620 | 1/1989 | Imran | 128/419 D |
| 4,821,724 | 4/1989 | Whigham | 128/419 P |
| 4,830,006 | 5/1989 | Haluska et al. | 128/419 PG |
| 4,869,252 | 9/1989 | Gilli | 128/419 PG |
| 4,878,497 | 11/1989 | Callaghan et al. | 128/419 PG |
| 4,940,054 | 7/1990 | Grevis et al. | 128/419 PG |
| 5,018,523 | 5/1991 | Bach, Jr. et al. | 128/419 PG |

*Primary Examiner*—Kyle L. Howell
*Assistant Examiner*—Kennedy J. Schaetzle
*Attorney, Agent, or Firm*—Gottlieb, Rackman & Reisman

[57] ABSTRACT

In an implantable antiarryhythmia pacemaker, an automatic cardiac arrhythmia detection and classification monitoring apparatus and method for measuring stimulated intracardiac electrogram potentials, deriving therefrom a paced depolarization integral (PDI), analyzing time-based changes in the PDI, detecting and classifying harmful cardiac rhythms while distinguishing harmful from benign tachycardias, and automatically establishing and initiating an appropriate therapy, if necessary, to revert the arrhythmia condition.

31 Claims, 10 Drawing Sheets

FIG. 13.

TCL = 300 ms
V-A = 70% TCL
= 210 ms

A-V = 10 ms
= 50 ms
= 100 ms
= 150 ms

TRAIN 1 N=4

| V-A 210 | A-V | V-A 210 | A-V | V-A 210 | A-V | V-A 210 | A-V |
|---|---|---|---|---|---|---|---|
|  | 10 |  | 10 |  | 10 |  | 10 |

TRAIN 2 N=4

| V-A 210 | A-V | V-A 210 | A-V | V-A 210 | A-V | V-A 210 | A-V |
|---|---|---|---|---|---|---|---|
|  | 50 |  | 50 |  | 50 |  | 50 |

TRAIN 3 N=4

| V-A 210 | A-V 100 | V-A 210 | A-V 100 | V-A 210 | A-V 100 | V-A 210 | A-V 100 |

TRAIN 4 N=4

| V-A 210 | A-V 150 | V-A 210 | A-V 150 | V-A 210 | A-V 150 | V-A 210 | A-V 150 |

APPARATUS AND METHOD FOR DETECTING ABNORMAL CARDIAC RHYTHMS USING EVOKED POTENTIAL MEASUREMENTS IN AN ARRHYTHMIA CONTROL SYSTEM

TECHNICAL FIELD

This invention relates to an apparatus and method for detecting, classifying, and treating abnormal cardiac rhythms. More particularly, the invention relates to implantable medical devices which monitor and control a patient's cardiac rhythm by sensing intracardiac electrograms, stimulating the heart with pacing pulses, measuring cardiac potentials evoked by these pacing pulses, deriving a parameter characteristic of the evoked potential, storing a history of evoked potential parameter values, and analyzing this history to detect and classify arrhythmias. Upon detection of an arrhythmia, these implantable medical devices automatically perform a therapy, such as one or more of the therapies of bradycardia pacing, antitachycardia pacing (ATP), defibrillation, and cardioversion, determined by the classification of the arrhythmia, to restore the heart's normal sinus rhythm. The invention is described herein as operating in a combined implantable antitachycardia pacing, bradycardia pacing, defibrillating or cardioverting arrhythmia control system. The invention may be incorporated in a device performing any one or more of these functions.

BACKGROUND OF THE INVENTION

As used herein, the term tachycardia refers to any fast abnormal rhythm of the heart which may be amenable to treatment by electrical discharges and specifically includes supraventricular tachycardia (SVT), atrial fibrillation and flutter (AF), ventricular tachycardia (VT), and ventricular flutter and ventricular fibrillation (VF).

Rubin's U.S. Pat. No. 3,857,398, dated Dec. 31, 1974, and entitled "Electrical Cardiac Defibrillator", describes a combined pacer/defibrillator. This device either performs a bradycardia pacing or a defibrillation function depending on the detection of a VT/VF. If a VT/VF is detected, the device is switched to the defibrillating mode. After a period of time to charge the capacitor, a defibrillation shock is delivered to the patient.

Improvements to this device were contained in a multiprogrammable, telemetric, implantable defibrillator which is disclosed in Gilli et al. copending patent application Ser. No. 239,624, filed Sep. 1, 1988, and entitled "Reconfirmation Prior to Shock in Implantable Defibrillator". The Gilli et al. device contains a bradycardia support system as well as a high energy shock system to revert ventricular tachycardias to normal sinus rhythm. On reconfirmation of the presence of a tachycardia, a shock is delivered to the patient at a predetermined time or when the desired energy level is reached.

As cardioversion or defibrillation shocks can be very unpleasant to a patient, especially when delivered frequently, it became necessary therefore to provide a device which included antitachycardia pacing therapy along with bradycardia support pacing therapy and defibrillation or cardioversion therapy, so that the implanted device could automatically provide the necessary therapy from a range of therapies offered by the device. Hence a further development in the field of combined implantable devices is described in U.S. Pat. No. 4,940,054, invented by Grevis and Gilli, dated Jul. 10, 1990, and entitled "Apparatus and Method for Controlling Multiple Sensitivities in Arrhythmia Control Systems Including Post Therapy Pacing Delay". This device is a microcomputer based arrhythmia control system which is programmable by means of a telemetric link. The device provides single chamber bradycardia support pacing, antitachycardia pacing, and cardioversion or defibrillation shocks for restoring normal sinus rhythm to a patient.

Additionally, various specific developments have been made in the field of tachycardia control pacers. Tachycardia is a condition in which the heart beats very rapidly, with a ventricular rate higher than 100 bpm and typically above 150 bpm, and an atrial rate as high as 400 bpm. There are several different pacing modalities which have been suggested for the termination of tachycardia. The underlying principle in all of them is that if a pacer stimulates the heart at least once shortly after a heartbeat, before the next naturally occurring heartbeat at the rapid rate, the heart may successfully revert to normal sinus rhythm. Tachycardia is often the result of electrical feedback within the heart. A natural beat results in the feedback of an electrical stimulus which prematurely triggers another beat. By interposing a stimulated heartbeat, the stability of the feedback loop is disrupted.

Langer et al., in U.S. Pat. No. 4,202,340, entitled "Method and Apparatus for Monitoring Heart Activity, Detecting Abnormalities, and Cardioverting a Malfunctioning Heart", describes an antitachycardia pacing system which detects VT/VF by deriving a probability density function from the analysis of the morphology or shape of intracardiac signals. This antitachycardia pacing system is subject to errors in the delivery of therapy due to the erratic and unpredictable nature of intracardiac signals.

The system disclosed in U.S. Pat. No. 4,475,551, entitled "Arrhythmia Detection and Defibrillation System and Method", invented by Langer et al. and issued on Oct. 9, 1984, illustrates arrhythmia detection in which the device first analyzes the probability density function to ascertain abnormal cardiac rhythms such as fibrillation, high rate tachycardias, and low rate tachycardias. Upon the discovery of such rhythms, the device senses heart rate so as to distinguish fibrillation and high rate tachycardia from low rate tachycardia. This device employs a predetermined threshold value for the rate which distinguishes such arrhythmia events. The inclusion of rate criteria to define arrhythmias was unable to remedy the deficiencies inherent in the probability density function operation; therefore the trend of later devices was to perform arrhythmia detection on the basis of rate information alone.

Geddes, in U.S. Pat. No. 4,291,699, entitled "Method and Apparatus for Automatically Detecting and Treating Ventricular Fibrillation" and issued on Sep. 29, 1981, characterizes a defibrillator which senses both the electrical and mechanical activity of the heart to detect fibrillation. This device measures the mechanical pumping action of the heart by detecting changes in electrical impedance between a pair of electrodes implanted within one of the ventricles of the heart. The diagnostic relevance of the impedance measurement requires an accurate assessment of electrical conduction volume within the heart. In devices which measure impedance using only two electrodes, gross volume approximation errors occur which lead to large inaccuracies in the impedance measurement. Furthermore, the diagnostic utility of the impedance measurement is degraded by extraneous influences on the impedance signal such as noise from respiration, changes in the patient's posture, and electrical interference.

A major disadvantage inherent in devices which detect cardiac arrhythmias on a basis of rate criteria alone is their propensity to inappropriately deliver shocks during physiological tachyarrhythmias or nonmalignant pathological tachyarrhythmias. In such devices, the rate standard cannot distinguish ventricular tachycardia or ventricular fibrillation from physiological tachycardia (also termed sinus tachycardia, herein) which normally arises from stress or exercise conditions and does not require antitachycardia pacing or defibrillation shock therapy. In addition, the rate criteria cannot differentiate VT or VF from the fast ventricular responses resulting from other pathological tachycardias such as supraventricular tachycardia or atrial flutter and fibrillation. Arrhythmia detectors using a rate basis are frequently confused by line frequency noise.

The use of antitachycardia pacing therapy in conjunction with a dual chamber pacing device is disclosed in the copending application of Norma L. Gilli, Ser. No. 462,499, filed Jan. 5, 1990, and entitled "Apparatus and Method for Antitachycardia Pacing in Dual Chamber Arrhythmia Control System", which application is assigned to the assignee of the present invention. In the Gilli application, upon detection of the presence of tachycardia, the tachycardia cycle length (TCL) is measured and a V-A interval less than or equal to the TCL is determined, along with an initial value A-V interval. Stimulation pulses are then delivered until the expiration of a given number (N) of V-A intervals and N A-V intervals, to complete a first train of pulses. A series of a given number (M) of trains of pulses similar to the first train of pulses is delivered, and the A-V delay interval is varied from the initial value thereof at least once prior to the completion of the series of M trains of pulses. Monitoring of intrinsic QRS complexes between pulse trains is performed. If the tachyarrhythmia is deemed to be accelerating, one operation of cardioversion or defibrillation is employed. The present invention is an improvement over said Gilli application with respect to the manner of detecting tachyarrhythmias.

SUMMARY OF THE INVENTION

In accordance with the present invention, the antiarrhythmia pacemaker generates a stimulating pulse to a patient's heart, then measures and processes cardiac potential signals evoked by the stimulating pulse to derive a paced depolarization integral (PDI) parameter. The PDI is a time integral of the depolarization voltage amplitude over the interval lasting essentially from the Q-point to the S-point of an evoked QRS complex. The pacemaker stores a time history of PDI measurements for a number of cardiac cycles and analyzes the current PDI measurement in light of this PDI time history to detect and classify cardiac arrhythmias. The pacemaker responds to malignant cardiac rhythms by delivering antitachycardia pacing pulses or defibrillation shocks.

The pacemaker detects and classifies tachyarrhythmias according to changes in PDI area and short-term uniformity. In particular, PDI analysis provides a means for distinguishing fibrillation from normal sinus rhythm and a means for discriminating pathological from physiological tachycardias.

Fibrillation, in both the atrium (AF) and ventricle (VF), is characterized by a rapidly oscillating intracardiac electrogram. During fibrillation, a stimulating pulse cannot generate an evoked response. Therefore, PDI measurements vary at random, depending on the point at which the pacemaker samples the fibrillation oscillation waveform. In general, averaged PDI measurements are smaller and less uniform (more variable) during fibrillation. The antitachyarrhythmia pacemaker characterizes fibrillation by the simultaneity of a large reduction in both mean PDI and PDI short-term uniformity.

To distinguish pathological from physiological tachycardia conditions, the pacemaker analyzes PDI changes by comparing averaged PDI values to PDI measurements obtained during conditions of normal sinus rhythm. Physiological VT decreases PDI and pathological VT increases PDI.

PDI's diagnostic utility for distinguishing physiological from pathological cardiac rhythms arises from changes in the sympathetic nervous system in response to a patient's metabolic needs or a substantial alteration in cardiac autonomic tone arising from another condition, such as excitement or fear. Physiological VT is accompanied by increase in sympathetic activity, elevating the concentration of catecholamines circulating in the blood and increasing cardiac contractility, venous blood return and end diastolic volume. These circulatory system transformations decrease the thickness of cardiac wall tissue. PDI value is most responsive to changes in cardiac conduction velocity and heart dimensions. A decrease in wall tissue thickness reduces the PDI value.

In contrast, pathological VT, which is not driven by a sympathetic response, is a malfunction of the heart's electrical conduction system, leading to a decline in conduction velocity. During pathological VT, disorganized electrical activity in the heart causes a decline in diastolic filling time and venous blood return, resulting in a diminished end diastolic ventricular dimension and compaction of the ventricular wall. This increased ventricular wall thickness, in combination with a decreased conduction velocity, causes an elevated PDI area measurement.

Upon detection of an arrhythmia, the pacemaker automatically performs a therapy determined by the classification of the arrhythmia, to restore normal sinus rhythm. Therapies include one or more of the therapies of bradycardia pacing, antitachycardia pacing (ATP), defibrillation, and cardioversion.

One objective of the preferred embodiment of the invention is to maximize the reliability of the arrhythmia detection decision-making process. Consequently, the pacemaker generates the stimulus and senses the signal in a manner which optimizes the diagnostic features of the evoked potential waveform. The pacemaker automatically adjusts the gain of its sensing amplifier to provide the best signal for arrhythmia diagnosis-a large signal without amplifier saturation. In addition, the system adjusts the stimulation amplitude to the smallest level which will assure successful stimulation, then monitors the heart's response to guarantee successful stimulation before performing the diagnostic measurement. The automatic stimulation amplitude function allows the pacemaker to compare similar signals over long time durations. The pacemaker also improves diagnostic reliability by performing automatic artifact reduction to minimize the size of the stimulation polarization artifact.

The ability to automatically reduce stimulation polarization artifacts is desirable in a system which analyzes the evoked potential because, in addition to generating a cardiac response, an electrical stimulus gives rise to a form of noise called the stimulation polarization artifact. When a pacemaker generates an electrical stimulus within the heart, it creates electrical charges which are stored in the body tissues. The stimulation polarization artifact is the signal arising from the dissipation of these stored charges. The amplitude of the stimulation polarization artifact is normally so much greater than that of signals arising from a natural heartbeat or the stimulated response that it is usually futile to sense these diagnostic signals until the stimulation polarization artifact charges dissipate. This is especially true when, as in the case of the preferred embodiment of the present invention, the pacemaker uses the same electrode for stimulating and sensing.

To rapidly dissipate these charges and minimize the stimulation polarization artifact at the pacing electrode, the pacemaker of the present invention generates stimulating pulses using a technique known as charge balancing. The procedure and circuit for performing charge balancing is disclosed in Whigham et al. U.S. Pat. No. 4,821,724, entitled "Pacing Pulse Compensation", which issued on Apr. 18, 1989, and refers to the method as active recharge. In this procedure, the pacemaker generates a triphasic stimulus, with the first and third phases being of one polarity and the second being of the opposite polarity. The amplitudes of the first and second phases are substantially proportional to each other. The third phase drives a current through the stimulating electrode until the voltage equals the starting quiescent voltage.

The charge balancing technique, also called the stimulation polarization artifact reduction technique, as performed by the preferred embodiment of the present invention, requires circuitry for sensing cardiac electrical activity including natural polarizations, evoked potentials and artifacts. This sensing circuitry is disclosed in U.S. Pat. No. 4,692,719, invented by R. H. Whigham, and entitled "Combined Pacemaker Delta Modulator and Bandpass Filter", which issued on Sep. 8, 1987. The disclosure of this patent is corporated herein by reference.

It is an object of the present invention to provide improved detection and classification of abnormal and pathological cardiac rhythms for the purpose of providing antitachycardia pacing therapy and defibrillation in an automatic implantable device.

It is a further object of the invention to provide antitachycardia pacing therapy with an improvement in cardiac arrhythmia detection and classification based on an analysis of cardiac evoked potential integrated depolarization gradients.

It is a still further object of the invention to provide antitachycardia pacing therapy with an improvement in cardiac arrhythmia detection and classification based on an analysis of a combination of heart rate and cardiac evoked potential integrated depolarization gradients.

It is another object of the invention to provide for improved distinguishing of pathological tachycardias from physiological tachycardias arising from increased metabolic demand or from a substantial alteration in cardiac autonomic tone due to another condition such as excitement or fear.

It is yet another object of the invention to provide improved rapid detection of ventricular or atrial fibrillation in order to provide for immediate initiation of shock therapy or atrial anti-fibrillation therapy, respectively.

It is a further object of the invention to provide for improved confirmation of the presence of ventricular fibrillation prior to initiating shock therapy.

It is a still further object of the invention to reduce the number or the necessity of defibrillation shocks given to a patient by preventing the development of VT's and AF's in a patient by means of enhanced maintenance of A-V synchrony and an improved method for distinguishing physiological from pathological cardiac rhythms.

In accordance with the principles of the present invention, there is, in an implantable antiarrhythmia pacemaker, an automatic cardiac arrhythmia detection and classification monitoring apparatus and method for measuring stimulated intracardiac electrogram potentials, deriving therefrom a paced depolarization integral (PDI), analyzing time based changes in the PDI, detecting and classifying harmful cardiac rhythms while distinguishing harmful from benign tachycardias, and automatically establishing and initiating an appropriate therapy, if necessary, to revert the arrhythmia condition.

Further objects, features and advantages of our invention will become apparent upon consideration of the following detailed description in conjunction with the accompanying drawings.

BRIEF DESCRIPTION OF THE DRAWINGS

FIG. 13 illustrates an embodiment of an antitachycardia pacing algorithm.

DETAILED DESCRIPTION

Figure 1:
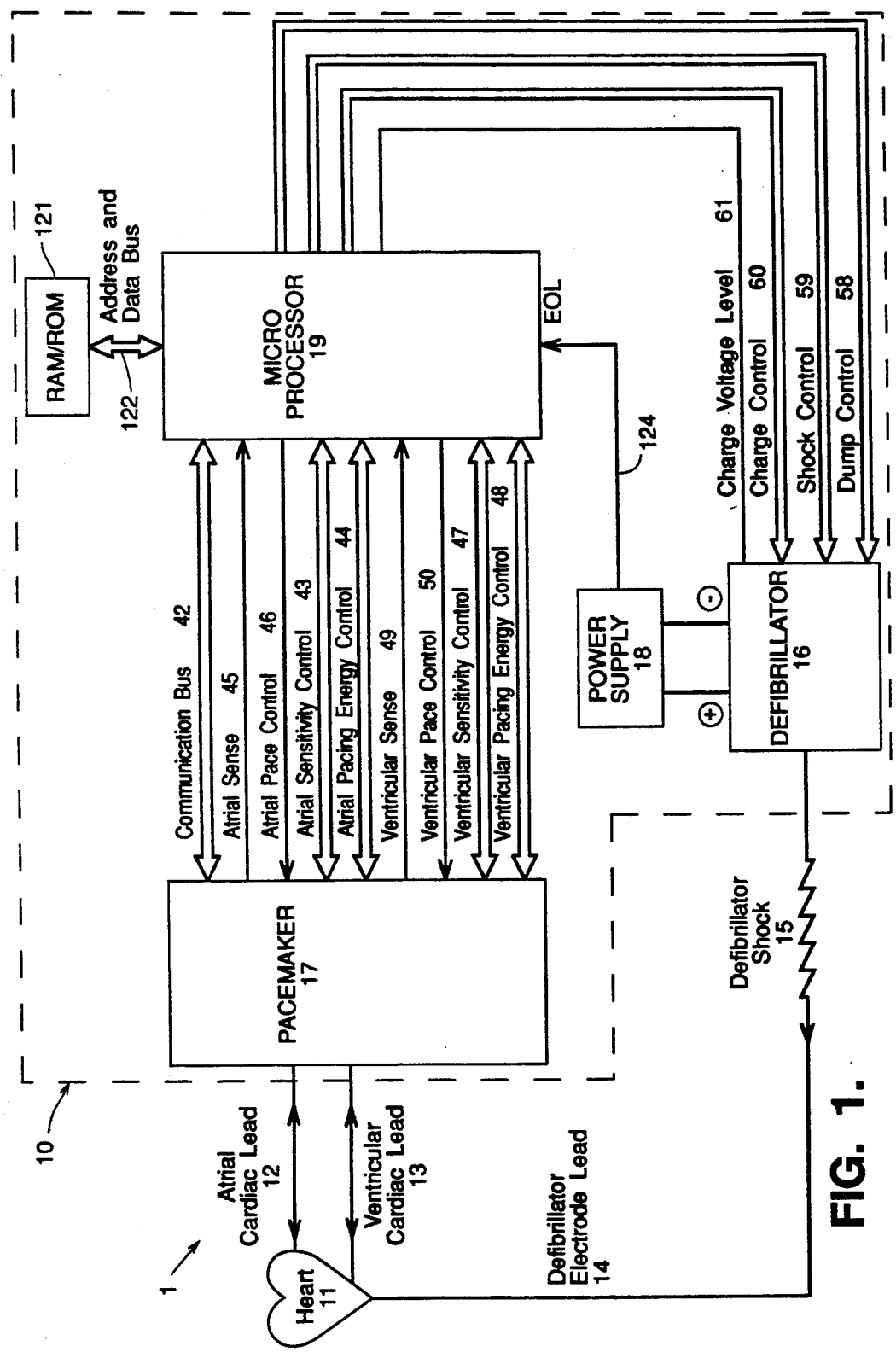
FIG. 1 is a block diagram of a dual chamber arrhythmia control system in accordance with the present invention.

Referring to FIG. 1, there is depicted a block diagram of an arrhythmia control system 1. System 1 is designed to be implantable in a patient and includes a pulse module 10 and appropriate leads for connecting module 10 to a patient's heart 11. More particularly, system 1 will generally include an atrial cardiac lead 12 extending to the atrium of the patient's heart for the administration of therapy to the atrium and a ventricular cardiac lead 13 extending to the ventricle of the patient's heart for the administration of therapy to the ventricle. System 1 generally also includes a pacemaker 17 for the detection of analog signals representing cardiac electrical activity and for the delivery of pacing pulses to the heart; a microprocessor 19 which, in response to various inputs received from the pacemaker 17 as well as from a defibrillator 16, performs various operations so as to generate different control and data outputs to both pacemaker 17 and defibrillator 16; and a power supply 18 for the provision of a reliable voltage level to pacemaker 17, microprocessor 19 and defibrillator 16 by suitable electrical conductors (not shown). Defibrillator 16 produces a high voltage to charge its capacitors and then discharges them in response to control signals from microprocessor 19. A defibrillator electrode lead 14 transfers the energy of a defibrillator shock 15 from the implanted pulse module 10 to the heart 11.

In particular, the microprocessor 19 determines the amplitude and morphology of the stimulating pulse and also sets the timing of pulse delivery. The microprocessor 19 sets the pulse delivery parameters for the purpose of charge balancing the stimulus output. The microprocessor 19 also governs the timing and number of intracardiac electrogram samples in addition to determining and executing any signal filtering required for signal analysis. As the microprocessor 19 performs signal sampling, it carries out the analysis necessary for the diagnostic purposes of the pacemaker, as described below.

Microprocessor 19 is connected to a RAM/ROM unit 121 by an address and data bus 122. An end-of-life (EOL) signal line 124 is used to provide, to microprocessor 19, a logic signal indicative of the approach of battery failure in power supply 18. As more fully described below, microprocessor 19 and pacemaker 17 are connected by a communication bus 42, an atrial sense line 45, an atrial pace control line 46, an atrial sensitivity control bus 43, an atrial pacing energy control bus 44, a ventricular sense line 49, a ventricular pace control line 50, a ventricular sensitivity control bus 47, and a ventricular pacing energy control bus 48. As also more fully described below, microprocessor 19 is connected to defibrillator 16 by a charge voltage level line 61, a charge control bus 60, a shock control bus 59, and a dump control bus 58.

Figure 2:
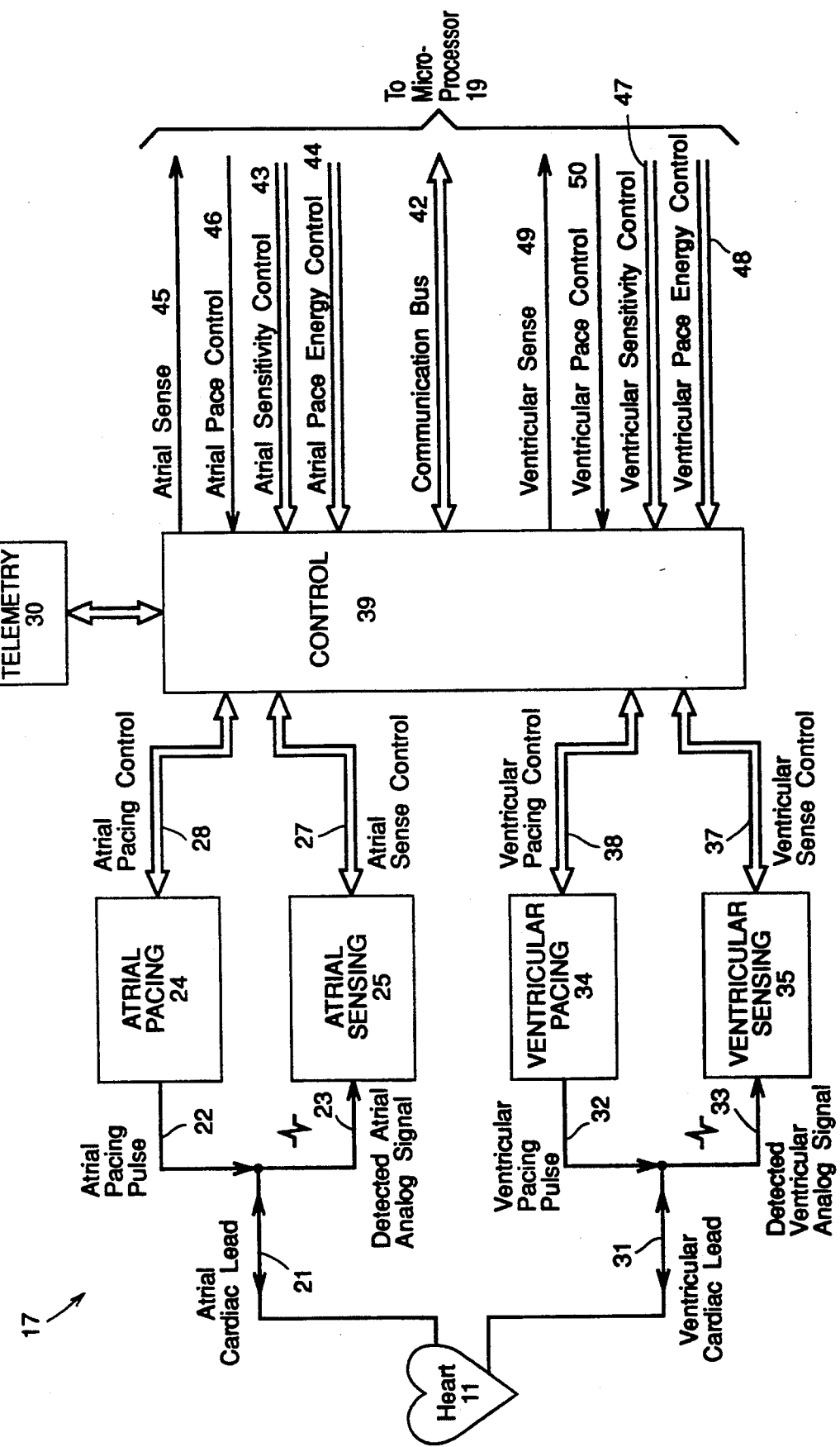
FIG. 2 is a block diagram of a pacemaker utilized in the system of FIG. 1.

Referring to FIG. 2, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit. As more fully described below, a change in this sensitivity affects the voltage deviation required at the sensing electrode for a sense to be registered. The operation of the logic which changes the sensitivity is described in greater detail in the aforesaid U.S. Pat. No. 4,940,054 of Grevis and Gilli, which description is incorporated herein by reference.

Atrial pacing circuit 24 receives from control block 39 via an atrial pacing control bus 28 an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to occur, while the atrial and ventricular pacing energy control inputs determine the respective magnitudes of the pulse energy. The operation of the logic which changes the pulse energy is described in greater detail in U.S. Pat. No. 4,869,252 of Norma Louise Gilli, issued Sep. 26, 1989, entitled "Apparatus And Method For Controlling Pulse Energy In Antitachyarrhythmia And Bradycardia Pacing Devices," which description is incorporated herein by reference.

The pacemaker 17 delivers a negative polarity stimulus through that conductor of the atrial cardiac lead 12 or ventricular cardiac lead 13 which has an electrical connection to the tip electrode of the lead. Other electrode connections of system 1 are its case (the electrical connection is with the physical case of the pacemaker) and the ring electrode of cardiac leads 12 and 13. The pacemaker 17 may connect in either a unipolar or bipolar fashion to the leads. When connected in a unipolar mode, the active electrode is at the lead tip, which is in contact with the cardiac tissue to be stimulated, and the indifferent electrode is the case of the implanted pacemaker 17. When connected in a bipolar mode, the indifferent electrode can be either the case or the ring electrode, which is an annular electrode on the lead a short distance from the tip electrode. Microprocessor 19 selects the mode of pacing and sensing by means of codes written to control block 39 via the communication bus 42. These codes determine the operative configuration of the pacemaker: bipolar, unipolar tip-case or unipolar ring-case. For purposes of analyzing evoked potentials, signals monitored when sensing intracardiac electrograms in the unipolar mode, which arise from cardiac potentials accumulated over a large surface of the heart, generally contain more information than signals sensed in the bipolar mode, thereby providing a more reliable diagnostic result. On the other hand, signals sensed in the bipolar mode offer better rejection of noise, including muscle and motion artifacts, and provide the most detailed signal description of the electrophysiological state from a localized region of the heart. It is to be understood that both the bipolar and unipolar configurations are within the scope of the invention.

Figure 3:
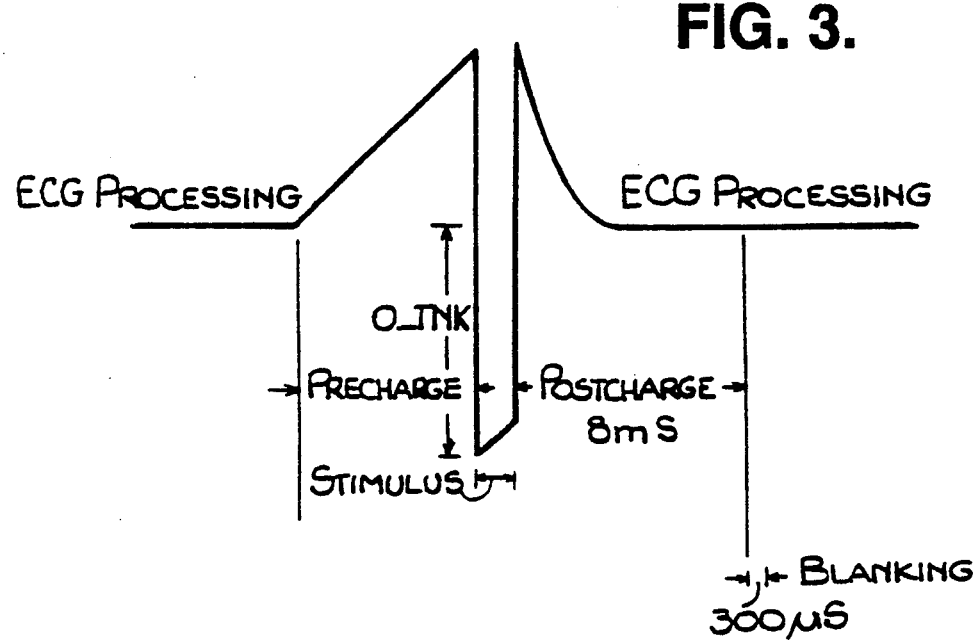
FIG. 3 depicts the form of a triphasic stimulation pulse generated by atrial pacing and ventricular pacing blocks of FIG. 2.

Atrial pacing block 24 and ventricular pacing block 34, in response to control codes issued by microprocessor 19 via control block 39, prepare for stimulation by storing electrical charge on capacitors and deliver the stimulating pulses, as described in U.S. Pat. No. 4,821,724, mentioned previously. These control codes determine the amplitudes, polarities and durations of the phases of the pacing stimulus pulses. FIG. 3 illustrates the four periods or zones of the pacing stimulus pulse: precharge, stimulus, postcharge, and blanking. It is to be understood that the waveform of FIG. 3 is not drawn to scale. Microprocessor 19 (FIG. 1) determines the duration of the precharge period, the postcharge interval duration (typically about 8 milliseconds), and the width of the negative portion of the stimulus pulse (usually in the range of 0.1 to 1.0 and commonly 0.5 milliseconds). After the stimulus pulse, an output generator times a blanking interval of about 300 microseconds to allow the circuit to settle after stimulation. The waveform of FIG. 3 represents the potential between the conductors of cardiac leads 12 or 13 of FIG. 1 and FIG. 2. One objective of the invention is for the microprocessor 19 to set the amplitudes and durations for these four periods in a manner to minimize the stimulation polarization artifact at the tip or pacing electrode in order to provide for reliable sensing of the heart's evoked potential resulting from a generated pulse.

Microprocessor 19 adjusts the precharge period to minimize the after-potential at the pacing electrode following the 8 millisecond postcharge duration. A postcharge duration of 8 ms is sufficiently short to permit sensing of the evoked potential. The adjusted precharge period, typically ranging in duration from 0 to 4 ms, varies from lead to lead and changes in time for a given lead.

Telemetry circuit 30 (FIG. 2) provides a bidirectional link between control block 39 of pacemaker 17 and an external device such as a programmer. It allows data such as the operating parameters to be read from or altered in the implanted module 10 (FIG. 1).

Figure 4:
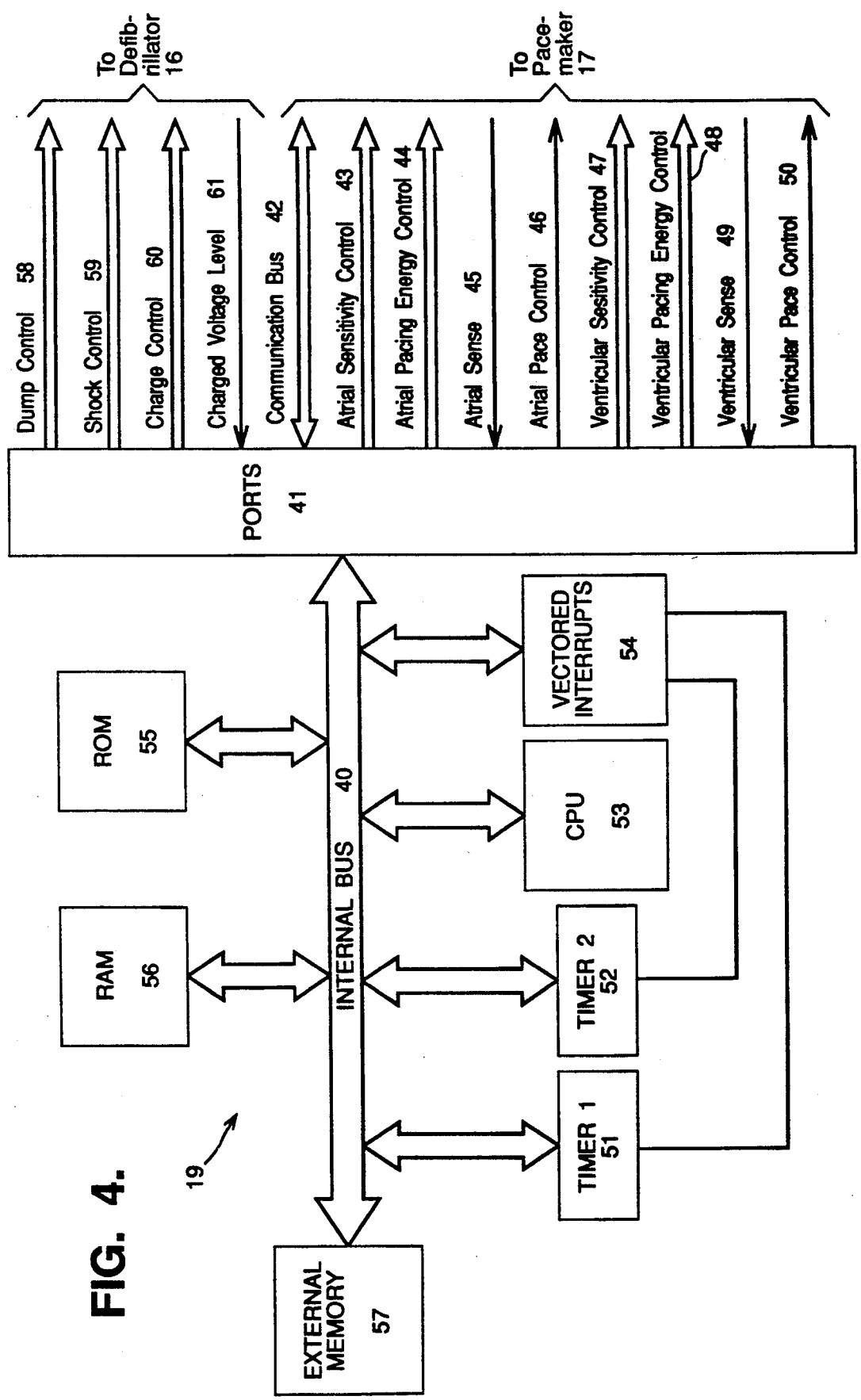
FIG. 4 is a block diagram of a microprocessor utilized in the system of FIG. 2.

Referring to FIG. 4, microprocessor 19 comprises two 16-bit timers 51 and 52, CPU 53, vectored interrupts block 54, ROM 55, RAM 56, external memory 57, ports 41 and an internal communications bus 40. RAM 56 acts as a scratch pad and active memory during execution of the various programs stored in ROM 55 and used by microprocessor 19. These programs include system supervisory programs, detection algorithms for detecting and confirming various arrhythmias, and programming for implementing the logic flow diagrams of FIG. 5, FIG. 6, and FIG. 7, as well as storage programs for storing, in external memory 57, data concerning the functioning of module 10 and the electrogram provided by ventricular cardiac lead 13 (FIG. 1 and FIG. 2). Timers 51 and 52, and associated control software, implement some timing functions required by microprocessor 19, normally without performing operations in software, thus reducing computational loads on and power dissipation by CPU 53.

Signals received from telemetry circuit 30 (FIG. 2) permit an external programmer (not shown) to change the operating parameters of pacemaker 17 by supplying appropriate signals to control block 39. Communications bus 42 serves to provide signals indicative of such control to microprocessor 19. Thus, it is also possible for an external programmer to control operation of defibrillator 16 by means of signals provided to microprocessor 19.

Appropriate telemetry commands may cause telemetry circuit 30 to transmit data to the external programmer. Data stored is read out, by microprocessor 19, on to communications bus 42, through control block 39 in pacemaker 17, and into telemetry circuit 30 for transmission to the external programmer by a transmitter in telemetry circuit 30.

Microprocessor 19 (FIG. 1) receives various status and/or control inputs from pacemaker 17 and defibrillator 16, such as the sense signals on sense lines 45 and 49. It performs operations, such as arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on lines 44 and 48, respectively, which determine the magnitude of the pulse energy, the shock control on line 59 which signals that a shock is to be delivered to the patient, the dump control on bus 58 which indicates that a shock is to be dumped at an internal load within the defibrillator, the charge control on bus 60 which determines the voltage level of the shock to be delivered, and the atrial and ventricular sensitivity controls on buses 43 and 47, respectively, which determine the sensitivity settings of the sensing circuits. Charge voltage level line 61 provides a digital signal representative of charge voltage from an analog-to-digital converter within defibrillator 16, thus providing a feedback loop which assures that a shock of proper energy level is delivered by defibrillator 16.

Figure 5:
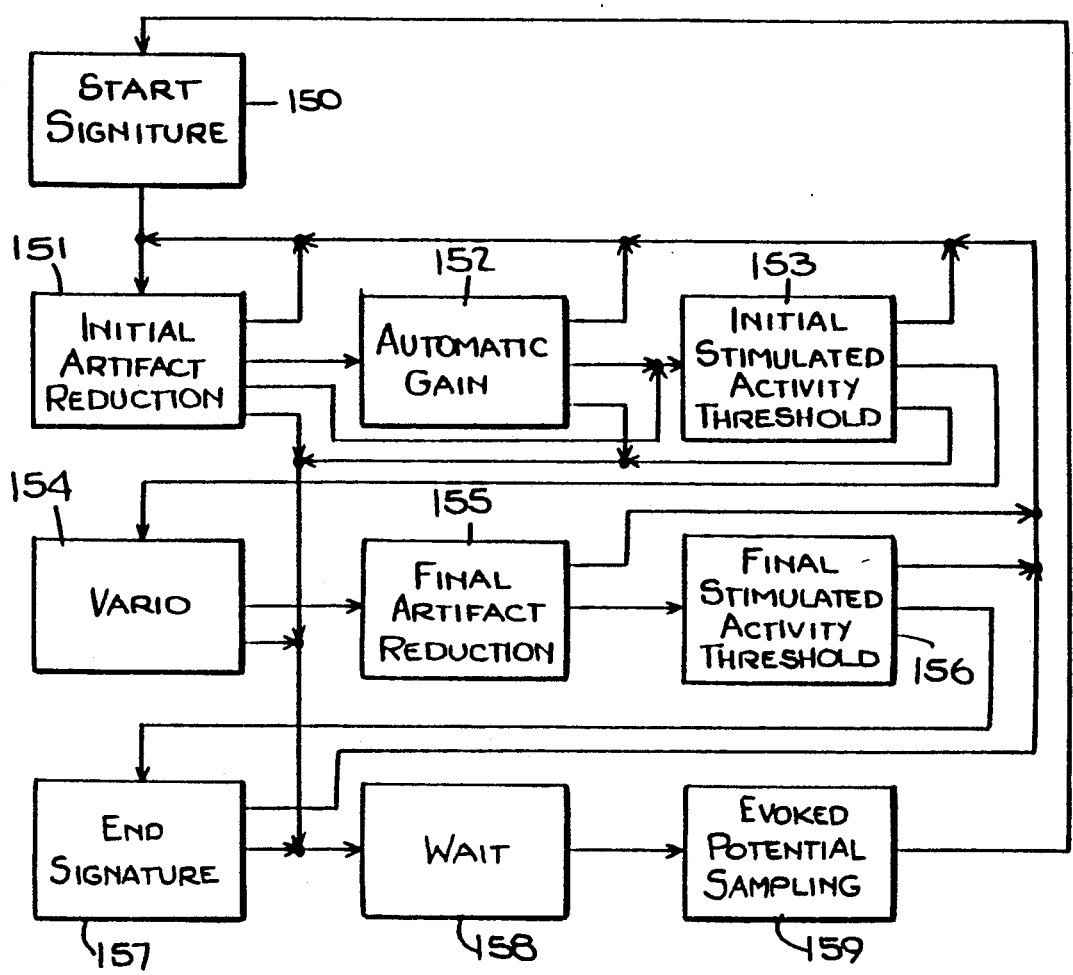
FIG. 5 is a flow chart illustrating a procedure for measuring the evoked potential, reducing the polarization artifact, setting sensing sensitivity (gain), and determining the minimum stimulation amplitude for safely activating the heart in the illustrative embodiment of the invention.

FIG. 5 is a flow chart illustrating a procedure, performed by pacemaker 17, for measuring the evoked potential, reducing the polarization artifact, setting sensing sensitivity (gain), and determining the minimum stimulation amplitude for safely activating the heart in the illustrative embodiment of the invention.

The best diagnostic evoked potential measurements are attained by reducing polarization artifacts to a level that is small in comparison to sensed evoked potentials and intrinsic cardiac events. Polarization reduction is called charge balancing because its goal is to determine such a balance of the charges delivered during the two positive phases and the single negative phase of the stimulus waveform as will result in an acceptably small polarization artifact.

The polarization artifact reduction procedure of FIG. 5 includes eight sub-procedures: start signature 150, initial artifact reduction 151, automatic gain 152, initial stimulated activity threshold 153, vario 154, final artifact reduction 155, final stimulated activity threshold 156, and end signature 157. After completing the polarization artifact reduction procedure, the system enters a wait state 158. Then, upon an activating event such as the timeout of a timer or detection of a potential abnormal cardiac rhythm by other procedures within the system, control procedes to an evoked potential sampling 159 sub-procedure. The preferred embodiment of the invention includes identical means for performing polarization artifact reduction procedures with respect to both the atrial and the ventricular heart chambers. It is intended that the invention may also be practiced in either heart chamber alone.

In the first seven sub-procedures (150 to 156), the arrhythmia control system 1 (FIG. 1) performs polarization artifact reduction and automatically adjusts the sensing amplifier gain and the stimulus pulse amplitude. These first seven sub-procedures are the polarization artifact reduction procedure which normally takes place when the heart has a normal or slow rate, rather than a heart rate associated with tachycardia or fibrillation. The system then overdrives the heart's natural rate to perform these seven sub-procedures. Finally, in the evoked potential sampling 159 sub-procedure, the pacemaker 17 measures the evoked potential as part of its arrhythmia detection function, at regular intervals and in response to abnormal cardiac rhythms. Normally, the pacemaker does not perform evoked potential sampling in every cardiac cycle but, rather, samples and calculates evoked potential control parameters at regular intervals (for example, every ten minutes) and for a predetermined duration (for example, one minute) to provide for measurement and storage of a set of normal evoked potential parameter readings. In addition, the presence of abnormal cardiac rhythms activates evoked potential measurement and analysis for as long as the abnormal rhythm endures.

Arrhythmia detection is comprised of two general operations, evoked potential analysis and cardiac rhythm analysis. It is standard in the art of cardiac pacemakers to measure the functional rate of the heart. Therefore, as an extension of the pacemaker's normal rate-tracking function, while performing the evoked potential sampling 159 sub-procedure, the pacemaker monitors heart rate.

The pacemaker 17 performs the rate portion of arrhythmia detection by sensing cardiac events, updating an X out of Y detector (the X/Y detector) to measure the time interval between consecutive cardiac events, and inserting this interval into a memory containing a history of such intervals. The pacemaker compares at least one element of this history of intervals with a predetermined detection interval. The pacemaker analyzes this history according to a preset X/Y detection criterion, X out of Y (for example, 8 out of 10 intervals). The cardiac rhythm meets this detection criterion when at least X of the Y most recent intervals are shorter than, or equal to, the detection interval. Arrhythmia detection includes detection limits for three types of arrhythmia events, listed in their order of priority: fibrillation, tachycardia, and the onset of tachycardia. When functioning in the evoked potential sampling 159 sub-procedure and, as a result of arrhythmia analysis, the pacemaker perceives a tachycardia or fibrillation event, it activates an evoked potential sampling procedure illustrated in FIG. 7. When the pacemaker detects a tachycardia rhythm, the pacemaker generates pacing stimuli for two purposes: to synchronize, or entrain, the heart's activity and to stimulate electrical activity for evoked potential analysis. Upon fibrillation detection, the pacemaker generates pacing pulses asynchronously with respect to heart activity, solely for performance of evoked potential analysis.

Pacemaker 17 initiates the polarization artifact reduction procedure portion of FIG. 5, beginning with the start signature 150 sub-procedure, upon the command of a telemetric communicator, or when activated by an internal timer, or in the event of failure of three consecutive generated pulses to evoke a cardiac response.

The start signature 150 sub-procedure provides notification, a signature stimulus, to one monitoring the cardiac signal that the pacemaker 17 is beginning an operation which automatically alters important stimulus parameters. A signature stimulus is two pulses which are separated by a short time interval (75 ms).

Next the pacemaker 17 performs the initial artifact reduction 151 sub-procedure to eliminate or reduce polarization artifacts and to provide a criterion for distinguishing a polarization artifact from an evoked cardiac depolarization. Here, the pacemaker generates a first stimulating pulse to incite a heart beat, samples an intracardiac electrogram following the pulse, calculates "activity" (a measurement of the heart's response) from the samples to determine whether the pulse was successful, and, if the pulse successfully excites the heart, generates a second pulse during the absolute refractory period of the heart. The pacemaker derives activity by sampling and integrating the intracardiac electrogram at 4 ms intervals, following the stimulus generation and its associated blanking period, for a sufficient period of time (e.g. 24 ms) for the heart's response to be detected.

Upon determining activity, the pacemaker 17 compares it to an activity threshold value derived in the most recent threshold operation (block 153 or 156 of FIG. 5). If activity is larger than the threshold value, the pulse successfully stimulated the heart. Otherwise, the pacemaker issues a backup pacing stimulus and overdrives the heart by increasing the pacing rate (for example, by 15 to 25 bpm) to avoid fusion beats (the combination of natural and stimulated cardiac activity). After three consecutive stimulus failures, the pacemaker restarts the initial artifact reduction sub-procedure 151, or terminates the procedure by delivering the end signature pulses in block 157 in the event of multiple such failures.

Following successful stimulated heart beats, the pacemaker 17 delivers the second pulse, called a refractory pulse, during the heart's refractory period (for example, about 125 ms after the stimulus pulse). At this time, any signal which arises represents primarily a polarization artifact, allowing the pacemaker to distinguish the polarization artifact from either stimulated or natural cardiac depolarizations. Following the refractory pulse, the pacemaker performs two sampling operations of the polarization artifact signal. In the first sampling operation, the pacemaker performs residual artifact sampling, following the trailing edge of the refractory pulse, using the same sampling procedure (4 ms samples acquired for 24 ms) as was performed while determining the activity following the stimulus pulse. In the second sampling operation, the pacemaker measures the polarization artifact to derive an artifact reduction parameter. The pacemaker performs an artifact reduction parameter accumulation on the first two or three samples acquired during the first sampling operation, in a manner similar to that done in connection with the integration to derive the activity, except that the artifact reduction parameter accumulation persists for two or three samples rather than six. Experimentally, these two or three samples were shown to characterize the peak amplitude of the first phase of a typically biphasic polarization artifact for the purpose of performing adjustments to reduce this artifact.

Figure 6:
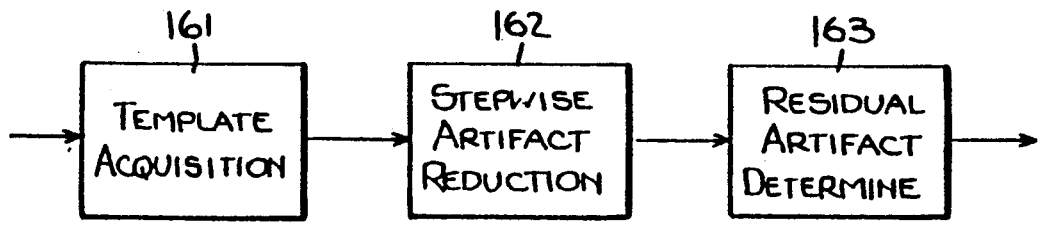
FIG. 6 is a flow chart illustrating operational steps by which a stimulation polarization artifact reduction function is accomplished by the illustrative embodiment of the invention.

In both artifact reduction sub-procedures (151 and 155), the pacemaker 17 performs the operations, shown in FIG. 6, of template acquisition 161, stepwise artifact reduction 162, and residual artifact determination 163. During template acquisition 161, the pacemaker measures the underlying intracardiac electrogram signal detected during refractory sampling in the absence of a refractory pulse. The purpose of stepwise artifact reduction 162 is to automatically adjust the precharge duration of the triphasic stimulus waveform (FIG. 3), to eliminate or reduce the polarization artifact. The pacemaker varies the precharge duration until the polarization artifact is small in comparison to the ventricular stimulated response. In the residual artifact determination 163 (FIG. 6), the pacemaker corrects the intracardiac electrogram signals measured following a refractory pulse to remove therefrom the underlying intracardiac electrogram signals which were sampled during template acquisition 161. The pacemaker then uses the resulting residual artifact parameter for pacemaker self-diagnosis and control, as will appear in greater detail below.

In the first template acquisition 161 operation, the pacemaker 17 initializes the precharge duration to the last successful value or to a preset value. The stimulus pulse amplitude and precharge duration remain unchanged throughout the template acquisition 161 and the stepwise artifact reduction 162 operations. The refractory pulse amplitude is zero volts during template acquisition 161, allowing the measurement of underlying electrogram signals occurring during the sampled portion of the heart's refractory period. The precharge durations for the stimulus and refractory pulses are the same. During template acquisition 161, the pacemaker measures, sums, and averages samples of the underlying intracardiac electrogram signal for eight cardiac cycles. In the aforesaid 24 ms sampling operation, the pacemaker creates a residual artifact template for correcting the residual artifact signal. In the 8 or 12 ms sample sampling operation, the pacemaker creates an artifact reduction template for performing stepwise artifact reduction. During stepwise artifact reduction 162, while generating both the stimulus and the refractory pulses in the triphasic waveform of FIG. 3 (precharge, stimulus, and postcharge), the pacemaker varies the precharge duration, maintaining a constant stimulus pulse amplitude, until the refractory polarization artifact is small in comparison to the ventricular stimulated response.

The pacemaker 17 samples and accumulates the artifact reduction parameter for each cardiac cycle, subtracts the artifact reduction template from the artifact reduction parameter, and adjusts the precharge duration by about 30 usec in the direction of the sign of the subtraction result. Because the polarization artifact represents a sensing amplifier's (not shown) response to an offset voltage (polarization) on the lead electrodes, the pacemaker 17 uses the polarity of the first phase of the artifact to determine which direction to change the precharge duration for the refractory pulse to further reduce the artifact amplitude. The precharge duration of the stimulus pulse remains unchanged at this time. The pacemaker 17 increases the precharge duration if the first phase of the polarization artifact is positive, otherwise it decreases the duration. The pacemaker limits both positive and negative precharge duration excursions to predetermined limits. At some point, depending on the sensing amplifier gain, stimulus energy, and characteristics of the electrode system, further changes in precharge duration will either completely eliminate the polarization artifact or cause it to reverse polarity. A polarization reversal occurs when the change in precharge duration causes the polarity of the first phase of the polarization artifact to change in sign as compared to the result of the previous cycle. After a predetermined number of polarization reversals (for example, four), the polarization artifact is sufficiently reduced and the pacemaker stores the newly determined optimum precharge duration. The pacemaker requires a number of polarization reversals to provide protection against incorrectly determining the proper precharge duration in the presence of fusion events.

During the residual artifact determination 163 operation, the pacemaker 17 sets the precharge duration of both the stimulus and the refractory pulses to the newly determined optimum precharge duration, and then measures and accumulates only the residual artifact value (not the artifact reduction parameter) for eight cardiac cycles. On the eighth cardiac cycle, the pacemaker 17 averages the accumulated residual artifact by dividing by eight, and subtracts from this average the residual artifact template determined by the previous template acquisition operation 161. This parameter is the template-corrected residual artifact.

Again referring to FIG. 5, after the successful completion of the initial artifact reduction 151, the pacemaker 17 performs the automatic gain 152 subprocedure to appropriately set the gain of the sensing amplifier for usage in atrial 25 and ventricular 35 sensing blocks of FIG. 2. The automatic gain 152 sub-procedure sets gain so that sensed signals will have a high amplitude, but not so high as to produce saturated signals. This improves the pacemaker's natural heartbeat signal sensing operation as well as its signal analysis capabilities while performing the other sub-procedures of FIG. 5. The pacemaker samples and stores intracardiac electrogram signal samples encompassing the QRS-complex, subtracts the previous sample from the current sample to determine the slope, detects the largest positive intracardiac electrogram slope in four consecutive paced cardiac cycles, compares this maximum amplitude to a predetermined automatic sensitivity test level, and increases or decreases the atrial or ventricular sensitivity setting by one count so as to set sensitivity so that the amplitude best approximates the test level. The automatic gain 152 sub-procedure continues until the amplitude crosses the test level a predetermined number of times (for example, four).

An alternate automatic gain 152 sub-procedure samples intracardiac electrogram signals resulting from natural heart activity rather than evoked potential signals. Rather than generating a pulse and sampling the evoked response, upon the sensing of natural heart activity, the pacemaker 17 samples intracardiac electrograms synchronized to the sensed event rather than to the stimulation pulse. The automatic gain procedure based on sensing of natural heart activity involves the determination of the largest absolute intracardiac electrogram slope rather than the largest positive slope, as in evoked potential sensing. Otherwise, the two sub-procedures are analogous.

The purpose of the stimulated activity threshold (153 and 156 of FIG. 5) operation is to measure the "threshold value", which is defined as the activity which distinguishes a stimulation pulse amplitude normally capable of generating a response by the heart from the activity of a stimulation pulse amplitude which does not. The pacemaker 17 initializes stimulus pulse amplitude to a predetermined level, then measures, accumulates, and averages activity over eight cardiac cycles. The pacemaker then performs a residual artifact test by comparing the magnitude of the corrected stimulated activity (the averaged activity minus the residual artifact obtained during the artifact reduction sub-procedure 151 or 155) to a preset multiple (for example, eight) of the magnitude of the residual artifact. If the magnitude of the corrected stimulated activity is too small, the system fails the residual artifact test since it is unable to sufficiently reduce the artifact. A residual artifact test failure may indicate a pacemaker malfunction or a physiological anomaly such as fusion events. If the averaged activity signal passes the residual artifact test, the pacemaker derives the threshold value by subtracting the residual artifact found in the last residual artifact determination operation (block 163 of FIG. 6) from the averaged activity and multiplying the result by a predetermined percentage factor (for example, 25%). This factor defines the minimum activity signal that will indicate a successful stimulation of the heart, taking into consideration the average signal level and the detected noise level (the residual artifact), and setting the threshold level between them.

After the successful completion of initial stimulated activity threshold block 153 (FIG. 5), the pacemaker 17 performs the vario 154 sub-procedure to determine the stimulation pulse amplitude normally capable of stimulating a response of the heart. For each vario cardiac cycle, the pacemaker measures activity. If the stimulus pulse stimulates a cardiac response, the pacemaker decreases the stimulation amplitude by a preset step size (for example, 0.1 V) for the next cardiac cycle. If the stimulus fails to evoke a response, the stimulation amplitude remains the same. After three consecutive failures or when the stimulus amplitude reaches a predetermined minimum value, the vario operation is complete and the pacemaker increases the stimulation amplitude by a preset voltage margin (for example, 1.0 V) and the pacemaker performs the final artifact reduction 155 sub-procedure.

The pacemaker 17 performs the final artifact reduction 155 and the final stimulated activity threshold 156 sub-procedures to minimize the magnitude of the polarization artifact and to determine the threshold value when stimulating the heart with pulses at the newly determined stimulation amplitude.

Upon completion of the various procedures 151 to 156, the end signature 157 sub-procedure provides notification to anyone monitoring the cardiac signal that the FIG. 5 operation is ending. The start (150) and end (157) signature operations are the same. Following the end signature 157 sub-procedure, the pacemaker 17 enters the wait state 158 to await one of the events which restarts the start signature 150 sub-procedure or activates evoked potential sampling 159 sub-procedure.

The pacemaker 17 performs the evoked potential sampling 159 sub-procedure, which is described in detail hereinafter in connection with the discussion of FIG. 7, only if the preceding operations and tests succeeded. The pacemaker analyzes evoked potentials, each cardiac cycle or in a predetermined proportion of cardiac cycles, while continuing to stimulate the heart at a rate which overdrives the heart's natural activity, and tests for successful cardiac stimulation. In the event of three consecutive failures to stimulate, the pacemaker 17 delivers a backup stimulation pulse, increases the stimulation pulse amplitude to a safe level, and restarts the polarization artifact reduction procedure.

Figure 8:
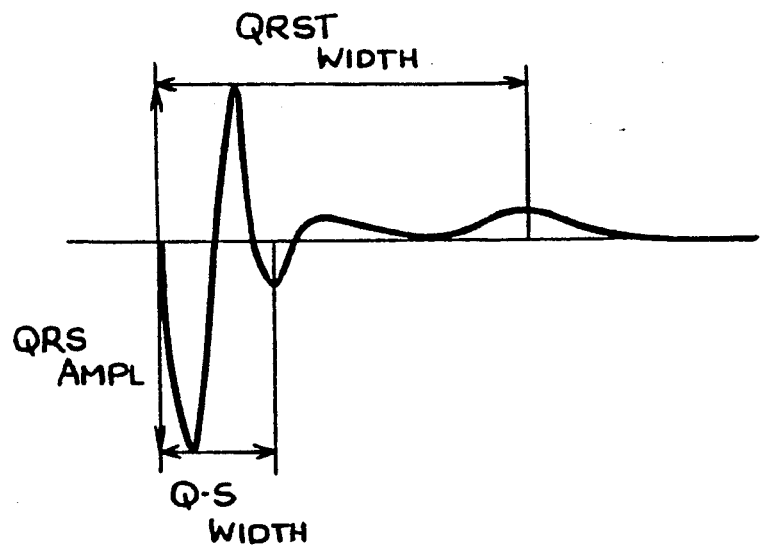
FIG. 8 is an illustration of a typical stimulated intracardiac electrogram QRST-complex waveform as detected by the pacemaker when it is sensing evoked potential signals in a unipolar mode.

FIG. 8 illustrates a typical stimulated intracardiac electrogram waveform as detected by the pacemaker 17 when it is sensing evoked potential signals in the unipolar mode. Pertinent measurements are labelled therein.

The term "evoked potential signal" is intended to refer to signals generated by the heart during the heart's activation wave in response to a stimulated pulse. It primarily refers to the heart's responsive QRS-complex.

For each measured cardiac cycle, the pacemaker 17 controls sampling and measurement of a paced depolarization integral (PDI), the temporal integral of the intracardiac electrogram where the integration begins following the stimulus and its blanking interval and the integration ends at the end of the depolarization of the heart (when the electrogram potential returns to zero). The pacemaker 17 determines the PDI in a similar manner to the activity derivation, by integrating samples of the intracardiac electrogram. One procedural difference between the PDI and the activity derivation ensues when sensing in the unipolar configuration. Instead of integrating for a fixed number of samples, the PDI determination requires the pacemaker to test the sample to find a zero value or the sample at which the intracardiac electrogram changes in sign from negative to positive, upon which sample the pacemaker will terminate the integration. The number of samples taken depends on the bandwidth of the sense amplifier in the atrial sensing 25 and ventricular sensing 35 blocks of FIG. 2. In addition to the PDI parameters, the pacemaker calculates a running average of PDI statistics, including sample mean and at least one short-term uniformity parameter. Various parameters: standard deviation, variance, minima and maxima for a preset number of cardiac cycles to signify short-term uniformity, and occurrences of PDI measurements below or above selected minima or maxima, provide an assessment of diagnostic short-term uniformity. The pacemaker measures and stores a time history record of PDI, PDI mean, and PDI short-term uniformity, for the purpose of detecting diagnostic changes over time.

Figure 7:
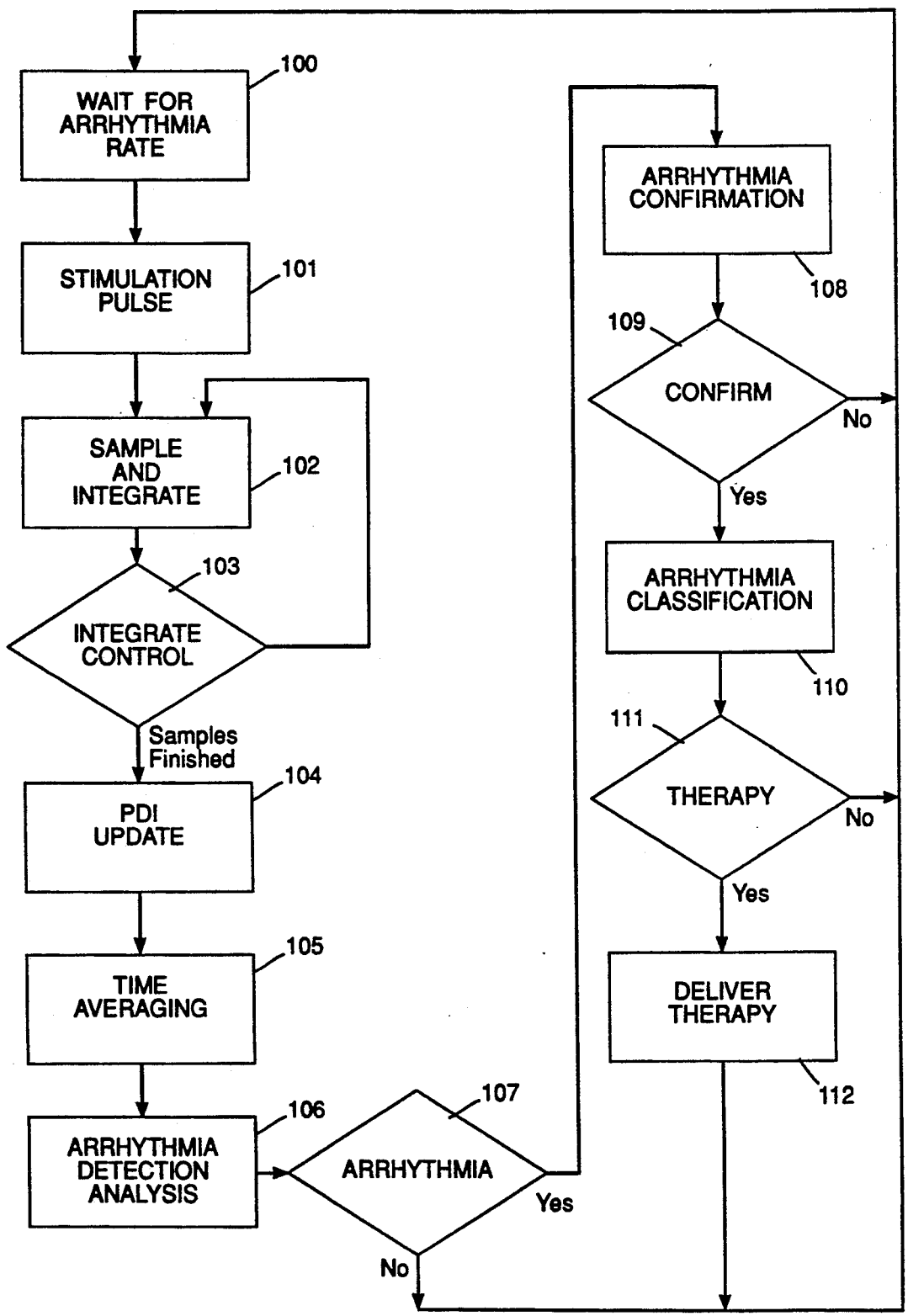
FIG. 7 is a flow chart illustrating operational steps by which an evoked potential sampling function is performed by the illustrative embodiment of the invention.

FIG. 7 is a flow diagram of the operations performed by the pacemaker 17, within a single cardiac cycle, to measure and analyze the PDI and its associated statistical parameters. The pacemaker continuously monitors the heart's intrinsic rhythm while performing standard pacemaker operations in wait for arrhythmia rate block 100. If the monitored heart rate is slower than a predetermined minimum, the pacemaker stimulates the heart at this minimum rate. The illustrative embodiment of the invention implements a combination of PDI and rate analysis to perform arrhythmia detection. Detection of an abnormal rate may be provided by means of the aforementioned X/Y detector, which activates evoked potential sensing and PDI determination. In addition to triggering an evoked potential analysis on the detection of a fast intrinsic heart rate, the pacemaker regularly samples evoked potential signals when the intrinsic rate is characteristic of normal sinus rhythm. The pacemaker then performs blocks 101 to 107 of FIG. 7 to derive a "normal" PDI parameter which is later used, upon detection of abnormal heart rates, as the comparison standard for detecting abnormal cardiac rhythms. Acquisition of a "normal" PDI parameter is triggered by a timer which is set to sample information at regular predetermined intervals.

When the pacemaker's rate monitoring analysis senses an abnormal rhythm and the possibility of a tachycardia or fibrillation condition, pacemaker 17 generates stimulation pulses in the heart and measures its evoked response to classify the arrhythmia and determine the proper corrective therapy. Whether the intrinsic heart rate is characteristic of tachycardia or of normal sinus rhythm, the pacemaker stimulates the heart by pacing at a 95% interval, in which a short-term average interval is determined and a timer is set to expire at the end of the determined interval. The pacemaker generates a stimulation pulse when the timer expires, unless an intrinsic event occurs prior to expiration of the timer. In this case, the pacemaker sets the timer for the next cardiac cycle to expire another 5% earlier. If the sensed rhythm is consistent with a tachycardia condition, the pacemaker generates stimulation pulses, which overdrive the heart's intrinsic rate of activity, at proper times according to known prior art antitachycardia pacing (ATP) techniques, and from the analysis of potentials evoked by these stimuli, the pacemaker determines whether a tachycardia is benign or harmful. For sensed rhythms indicative of fibrillation, the pacemaker generates pacing pulses out of synchrony with respect to the heart's activity.

One of the advantages of a pacemaker 17 which detects tachycardias on the basis of evoked potential analysis is that fewer cardiac cycles are required for testing in X/Y detection. For example, instead of requiring 8 of 10 tachycardia rate cycles, which are required in the absence of evoked potential analysis to safely define a tachycardia condition, the pacemaker can properly designate a tachycardia condition on the basis of 3 of 4 accelerated cycles. Because evoked potential analysis provides for faster tachycardia detection, the pacemaker can initiate a tachycardia reversion therapy earlier, thereby enhancing the effectiveness of the therapy.

In an alternative embodiment of the invention, the pacemaker 17 detects an arrhythmia rate by measuring the intrinsic cardiac rate every cardiac cycle if such rate is higher than a minimum predetermined pacing rate. This embodiment of the pacemaker triggers evoked potential measurement and analysis for any detected cycle duration that is shorter than a predetermined minimum interval (for example, 600 msec). This approach eliminates the X/Y detector and provides for tachycardia detection without requiring a physician to estimate a tachycardia rate. This is important because no particular heart rate exists which can accurately define the presence of a pathological tachycardia condition. In addition, eliminating the X/Y detector speeds the response time of the antitachycardia pacemaker because X/Y detection inherently slows detection of a tachycardia.

After the pacemaker 17 generates a stimulation pulse in block 101 of FIG. 7, it samples the intracardiac electrogram at 4 ms intervals to detect the heart's response, then digitally integrates the sample values and stores the result. Also in stimulation pulse block 101, the pacemaker initializes the integral accumulator memory. Each sample has a signed value indicating the polarity of the waveform. The stimulated depolarization waveform, the signal of interest according to the invention, is always negative immediately following the stimulus. Therefore, the pacemaker complements the sample value before storing and performing the integration to simplify logical and arithmetic operations.

Figure 9:
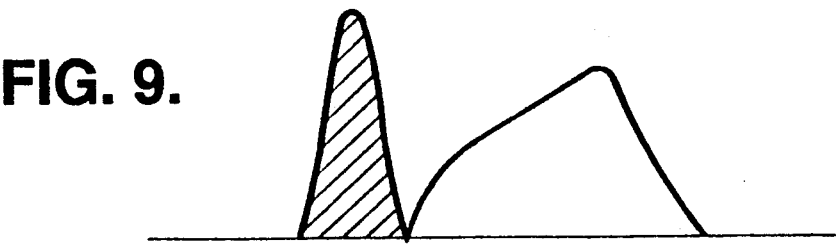
FIG. 9 is an illustration of the morphology of a unipolar sensed, stimulated intracardiac electrogram waveform as to which the Q-S width portion has been integrated, highlighting the integrated depolarization waveform.

The pacemaker 17 performs sampling, integrating, and storing operations for 4 ms samples in sample and integrate block 102. Integration control block 103 performs the logic for terminating the sampling of block 102. Sampling and integration continue so long as the sign of the stimulated waveform remains negative. Later, the waveform sample becomes positive, indicating repolarization of the cardiac tissue, as shown in FIG. 8. The absolute value of the integral of the intracardiac electrogram from the stimulus to the zero crossing prior to repolarization is the area of the depolarization waveform, called the paced depolarization integral (PDI), as is illustrated by the shaded area in FIG. 9. In integration control block 103, the pacemaker searches for the point of change from depolarization to repolarization. The change from depolarization to repolarization is that one of the waveform samples which switches in sign from negative to positive. In FIG. 8, this point occurs at the end of the portion of the waveform denoted as the Q-S width for the unipolar mode.

Because a noisy intracardiac electrogram signal may have a number of these zero-crossing occurrences, the pacemaker requires some means to define a valid polarization change. The preferred embodiment of the invention defines a window, specified as the "depolarization window", in terms of the earliest and the latest sample following the stimulus pulse within which the polarization may change from negative to positive. The zero crossing point within the window defines the end of depolarization. The pacemaker performs two tests to find the end of depolarization in integration control block 103. If the sample is negative prior to its updating for the current sample and becomes positive after updating and the sample number is within the range previously defined as the depolarization window, then control proceeds to a PDI update block 104. The procedure also terminates evoked potential sampling and proceeds to block 104 if the sample number is the last in the window. Otherwise, the pacemaker continues to perform the sampling and integration of block 102. The predetermined window boundaries may vary according to the rate of sensed cardiac activity. For example, because stimulation during fibrillation conditions does not evoke a cardiac response, the presence of a zero crossing may occur at random in the sampled intracardiac electrogram waveform. In this case, the pacemaker may sample for a predetermined duration without regard to the presence of zero crossings.

In PDI update block 104, the pacemaker saves PDI parameters resulting from the operations of blocks 102 and 103 in the current cardiac cycle. The pacemaker loads the current sample PDI (after it was updated in block 102) and stores it into a cycle PDI memory location. Also, the pacemaker stores the current sample number, which is a count of the number of samples following the stimulation pulse, into a cycle depolarization duration memory location. The pacemaker derives and stores another parameter, a cycle PDI amplitude to duration ratio, by dividing the current PDI by the current depolarization duration.

For each of the current cycle parameters derived and stored in block 104 (PDI, depolarization duration, and PDI amplitude to duration ratio), the pacemaker performs time averaging in block 105. In general, changes in the statistical mean and/or short-term uniformity of the PDI are useful for discriminating between fibrillation, tachycardia, and sinus rhythm in both the atrium and the ventricle. Short-term nondiagnostic changes in the evoked potential waveform parameters, arising from day to day (20% changes are not uncommon) and circadian rhythm variability, as well as randomness arising from external influences such as positional shifts, drug therapy and fusion events, impede the detection and characterization of arrhythmias. In addition, long-term drift in waveform parameters creates uncertainty in arrhythmia diagnosis.

The system 1 addresses both short and long-term variability problems by averaging the data using lowpass filtering techniques. For each acquisition of parametric data, the pacemaker 17 lowpass filters the data on a short-term basis to provide an averaged characterization of the parametric data over roughly the last fifteen seconds, and further lowpass filters the data on a long-term basis to characterize the parametric data over about a four day period. Because the purpose of long-term filtering is to set normal standards for evoked potential parameters, long-term filtering takes place only when regular timed intervals, rather than arrhythmia detection, activate evoked potential analysis. The pacemaker then compares the short-term with the long-term parametric data averages. If the parametric data average changes by more than a predetermined threshold value, the pacemaker stores a code in memory designating the nature and time of the test result and initiates an analysis of PDI parameters in combination with the history of cardiac rhythm, ultimately leading to control of an appropriate therapy.

In addition to determining the long and short-term averages of the described parameters in block 105, the pacemaker 17 computes a PDI short-term uniformity value. Average deviation is one example of a short-term PDI uniformity parameter, in which the pacemaker subtracts the PDI value for the current cardiac cycle from the long-term PDI average, then averages the absolute value of the subtraction result. Similarly, the pacemaker subtracts the current short-term PDI average from the long-term average to provide a measurement of uniformity. Another example of a short-term uniformity indicator is provided by a thresholding operation, in which the pacemaker compares the PDI measurement for the current cardiac cycle with one or more preset threshold values. If the current PDI measurement is within a range associated with non-uniformity, the pacemaker stores a record of this occurrence. For example, the pacemaker can store a history of threshold test results from recent cardiac cycles. The occurrence of A out of B cardiac cycles outside the range of uniformity, with preselected values of A and B, is one factor in arrhythmia detection and classification.

The pacemaker 17 performs short-term and long-term average filtering in block 105 using recursive filtering techniques which are well-known in the art of signal processing. The short-term filter memory is described by the following equation, in which PDIst represents a short-term filter accumulator, X is an updating data parameter and i represents the current cycle:

$$PDIst_i = 63/64 \times PDIst_{i-1} + X_i.$$

The long-term filter accumulator memory, PDIlt, is described by the following equation:

$$PDIlt_i = \frac{127}{128} \times PDIlt_{i-1} + PDIst_i.$$

Also in block 105, the pacemaker may derive uniformity measurements to assist in detection of fibrillation, using recursive filtering techniques. The short-term uniformity filter memory is described by the following equation, in which DIFst represents a short-term filter accumulator for variability from PDIst and X is the updating data parameter:

$$DIFst_i = \frac{63}{64} \times DIFst_{i-1} + abs(X_i - PDIst_i).$$

The long-term uniformity filter memory, DIFlt, is described by the following equation:

$$DIFlt_i = \frac{127}{128} \times DIFlt_{i-1} + DIFst_i.$$

After processing the data in time averaging block 105, the pacemaker 17 analyzes the processed data in arrhythmia detection analysis block 106 for the purpose of detecting cardiac arrhythmias. After updating the short-term and long-term averages, the pacemaker compares the short-term PDI (PDIst) with the long-term PDI (PDIlt) values and analyzes the result of this comparison with heart rate data.

Figure 10A:
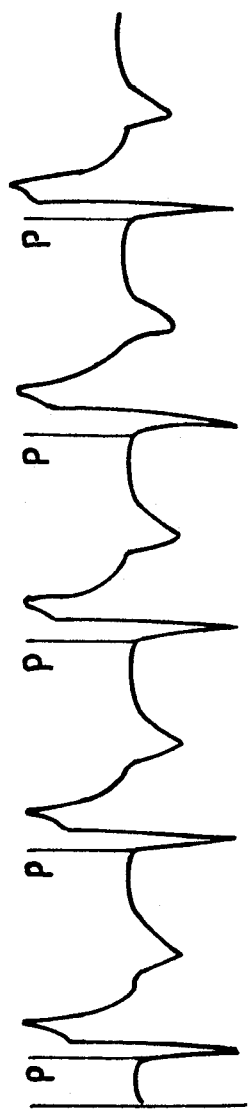
FIGS. 10A, 10B, 10C, and 10D are sample illustrations of the morphology of stimulated intracardiac electrogram waveforms under normal conditions (FIG. 10A), fibrillation (FIG. 10B), physiological tachycardia (FIG. 10C), and pathological tachycardia (FIG. 10D)
Figure 10B:
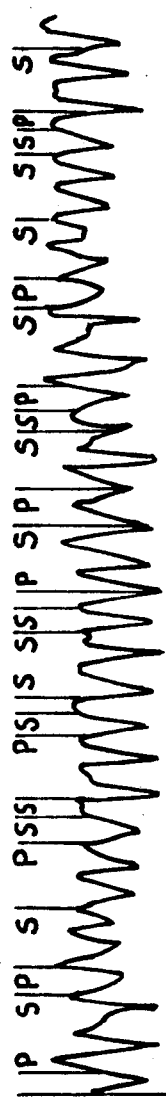
Figure 10C:
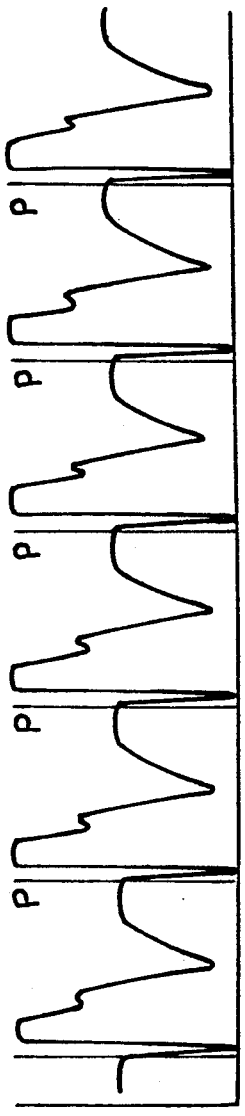
Figure 10D:
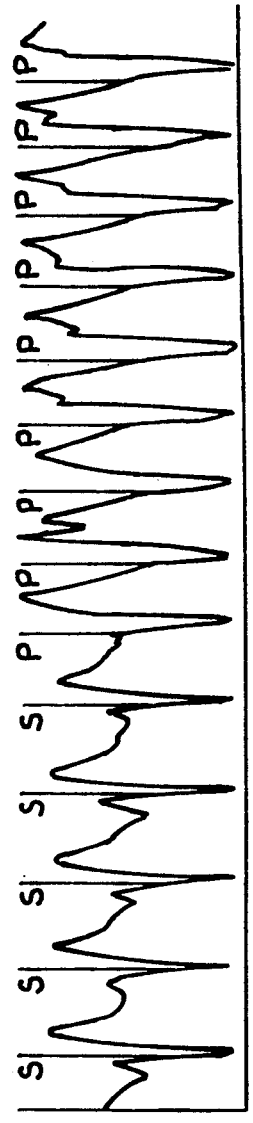

The purpose of the arrhythmia detection control parameter is to detect cardiac arrhythmias through changes in the intracardiac electrogram waveform. FIGS. 10B-10D illustrate the type of changes in the paced, in comparison with the overdriven paced normal sinus rhythm (FIG. 10A), which result from arrhythmia, including alterations arising from fibrillation (FIG. 10B), physiological tachycardia (FIG. 10C), and pathological tachycardia (FIG. 10D). Each "P" notation designates the timing of pacing pulses and each "S" notation signifies intrinsic cardiac event sensing.

Figure 11C:
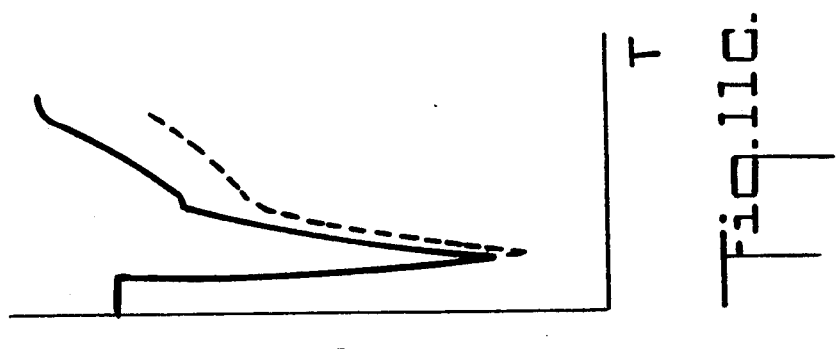
FIGS. 11A, 11B, and 11C are sample illustrations of the morphology of paced depolarization integral (PDI) waveforms comparing normal conditions to each of fibrillation (FIG. 11A), physiological tachycardia (FIG. 11B), and pathological tachycardia (FIG. 11C)
Figure 11B:
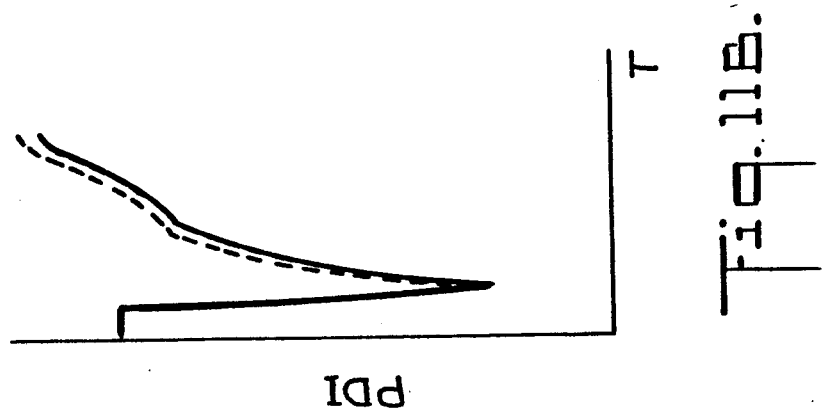
Figure 11A:
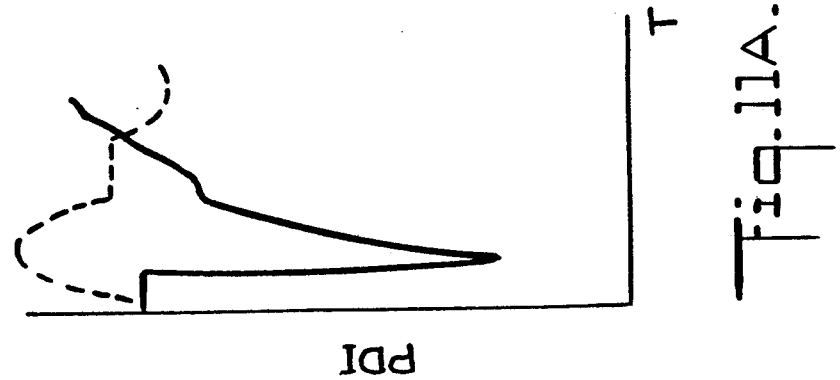

FIGS. 11A, 11B, and 11C illustrate changes in the morphology of paced depolarization integral (PDI) waveforms in which each solid line depicts a normal PDI waveform and each broken line represents PDI waveforms consistent with conditions of fibrillation (FIG. 11A), physiological tachycardia (FIG. 11B), and pathological tachycardia (FIG. 11C).

Referring to block 106 of FIG. 7, the pacemaker 17 performs arrhythmia detection analysis, which is a preliminary screening for discerning the possibility of fibrillation or tachycardia based on heart rhythms and PDI parameters. If the history of cardiac events meets the criteria for more than one type of arrhythmia, the device classifies the event according to the higher priority. Each of these types of arrhythmia events is comprised of one or more classifications, each of which is associated with a predetermined pacing therapy.

In one operation of arrhythmia detection analysis block 106, a fibrillation detector recognizes the possibility of fibrillation, either atrial fibrillation (AF) or ventricular fibrillation (VF) according to the heart chamber in which the evoked potentials are measured. The fibrillation detector is activated when the previously discussed X/Y detector criterion is met when comparing the current heart rate with a predetermined fibrillation detection interval (FDI). In the preferred embodiment of the invention, FDI is a fixed value of 250 ms and the X/Y detector criterion is 8 short intervals out of 10 cardiac cycles in adult human beings. If the cardiac rhythm meets the X/Y detection criterion for fibrillation, the short-term average PDI (PDIst) is less than a predetermined percentage (for example, 25%) of the long-term average PDI (PDIlt), and the short-term PDI uniformity (DIFst) is larger than a predetermined multiplication factor (for example, 1.25) times the long-term PDI uniformity (DIFlt), then the pacemaker 17 performs rapid discrimination of fibrillation and immediately performs therapy to revert the pathological condition. The uniformity measurement is a reliable indicator of fibrillation in both the atrium and the ventricle and is most important for distinguishing fibrillation from other rhythms.

Upon detection of ventricular fibrillation, the pacemaker 17 responds with shock therapy. Detection of atrial fibrillation activates generation of defibrillation pulses in the atrium, synchronized to ventricular activity, to revert the condition. If the X/Y detection criterion is met and PDIst is not less than the predetermined percentage of PDIlt, then an arrhythmia condition exists (shown by a "yes" condition of arrhythmia logic block 107) and the pacemaker performs arrhythmia confirmation block 108.

In a second operation of arrhythmia detection analysis block 106, a tachycardia detector identifies the possibility of a tachycardia condition when the cardiac rate meets the X/Y detector criterion by comparing a recent history of cardiac intervals to a predetermined Tachycardia Detection Interval (TDI). Values of TDI range from 300 to 600 milliseconds, defining tachycardia rates from 200 to 100 bpm, respectively. The tachycardia detector analyzes cardiac rhythms according to heart rate and PDI evaluation, but without regard to how fast the cardiac rate accelerates. A tachycardia may be either pathological or physiological. A physiological tachycardia occurs when the patient is exercising, frightened, or excited. An alternative embodiment of the invention identifies the possibility of a tachycardia condition by determining whether an intrinsic cardiac cycle length is shorter than a predetermined minimum. This embodiment does not require an X/Y detector.

Evoked potential analysis assists in distinguishing pathological tachycardias from physiological tachycardias. An increase in mean PDI (PDIst) in comparison with normal sinus rhythm PDI (PDIlt) is indicative of pathological tachycardias. For physiological tachycardias, PDIst decreases or remains the same in comparison to PDIlt. Therefore, if PDIst is greater than PDIlt by a predetermined percentage (for example, 30%) and the cardiac interval is shorter than TDI in X of Y cardiac cycles (for example, 8 of 10), then an arrhythmia condition exists (shown by a "yes" condition of arrhythmia logic block 107) and the pacemaker classifies the condition as a possible tachycardia and performs arrhythmia confirmation block 108.

In a third operation of arrhythmia detection analysis block 106, a tachycardia onset detector identifies the possibility of the onset of a tachycardia condition upon perceiving the combination of an increased PDI and a sudden and sustained increase in heart rate. A pathological tachycardia rhythm arises suddenly, often within two cardiac cycles. In contrast, a physiological tachycardia gradually increases in rate, usually accelerating one or two bpm per cardiac cycle.

The tachycardia onset detector first performs X/Y detection, comparing the interval history with an Onset Detection Interval in the range of 300 to 600 milliseconds to ascertain whether a decrease in interval length is sustained. ODI is normally a longer interval than TDI, to provide, by means of the tachycardia onset detector, faster pathological tachycardia detection and response. The amount of decrease in interval length (Delta), and the number of cardiac cycles within which the decrease occurs, have predetermined values. The preferred embodiment of the ODI calculates the average interval in the interval history using one or more cardiac interval samples preceding the Y intervals defined by the X/Y detector. This provides a reference value against which the tachycardia onset detector measures changes of interval. Upon meeting the change in interval criterion, the X/Y detector then ascertains that all Y intervals remain at least Delta shorter than the calculated average interval and that at least X out of Y intervals are also shorter than or equal to ODI.

The tachycardia onset detector, similar to the tachycardia detector, employs evoked potential analysis to assist in distinguishing pathological tachycardias from physiological tachycardias. A cardiac rhythm which meets the X/Y detector criterion (for example, 12 of 15 or 16 of 20) for onset detection is more likely to be a pathological tachycardia than a rhythm which passes the tachycardia X/Y detector test. The purpose of PDI analysis in the context of onset detection is to prevent preliminary classification of obvious physiological tachycardias as pathological tachycardias. Therefore, after meeting the X/Y detector criterion for onset, an arrhythmia condition exists (shown by a "yes" condition of arrhythmia logic block 107) and the pacemaker 17 classifies the condition as a possible tachycardia and performs arrhythmia confirmation block 108 in nearly all cases. Only when PDIst decreases in comparison to PDIlt and decreases by a predetermined percentage (for example, 10%), does the pacemaker 17 reclassify the condition as a non-arrhythmia event in arrhythmia logic block 107, after which pacemaker control returns to wait for arrhythmia rate block 100.

In fourth operation of arrhythmia detection analysis block 106, an asystole detector distinguishes asystole from ventricular fibrillation which the pacemaker has otherwise failed to detect due to undersensing of cardiac signals. Asystole is the absence of a heartbeat. It is also called cardiac standstill or arrest. When there is no sensed cardiac rhythm, the pacemaker provides bradycardia backup pacing at a predetermined pacing rate. When the pacemaker is pacing at this rate and the short-term PDI and PDI uniformity maintain their non-arrhythmia values (for example, PDIst remains larger than 75% of PDIlt and DIFst remains smaller than 1.25 times DIFlt), then the pacemaker classifies the event as asystole and continues to generate pacing stimulus pulses at the predetermined rate. Otherwise, if the pacemaker is pacing at the predetermined rate but the PDI measurements indicate a failure to stimulate the heart, the pacemaker classifies the rhythm as the possibility of VF.

In arrhythmia confirmation block 108, the antiarrhythmia pacemaker 17 confirms the presence of tachyarrhythmia before delivering each ATP train or cardioversion/defibrillation shock. Tachyarrhythmia confirmation employs an X/Y detector as previously described. Each confirmation test requires redetermination of the tachyarrhythmia confirmation interval (TCI) for comparison with the current interval by the X/Y detector. The operational value of the TCI depends on the identity of the detector which discerned the tachyarrhythmia. Initiation by the tachycardia onset detector causes the device to calculate TCI dynamically, setting TCI to the average interval before onset less a fraction of Delta (for example, one-half). Otherwise, the device sets TCI equal to TDI. In either case, TCI is limited to values between ODI and TDI.

If the pacemaker 17 fails to confirm an arrhythmia condition in block 108, confirmation logic block 109 directs pacemaker control to wait for arrhythmia rate block 100. Otherwise, upon confirming the presence of tachyarrhythmia but prior to delivering therapy, the pacemaker classifies the tachyarrhythmia to determine the appropriate therapy in arrhythmia classification block 110. Classification is based on analysis using the X/Y detector in conjunction with two intervals having predetermined durations, a minimum tachycardia cycle length for antitachycardia pacing (TCLminATP) and a maximum tachycardia cycle length for defibrillation (TCLmaxD). TCLminATP represents the tachycardia cycle length below which intervals are too short for antitachycardia pacing to be effective. TCLmaxD represents the tachycardia cycle length below which the patient is likely to be hemodynamically compromised by the tachyarrhythmia and antitachycardia pacing is likely to be ineffective. It therefore requires shock therapy. Note that TCLmaxD must always be greater than TCLminATP. There can be no range of interval lengths which are too short for antitacycardia pacing but too long for shock therapy. The range of allowable values for TCLminATP and TCLmaxD is illustrated by the lower and upper broken lines in FIG. 12.

Figure 12:
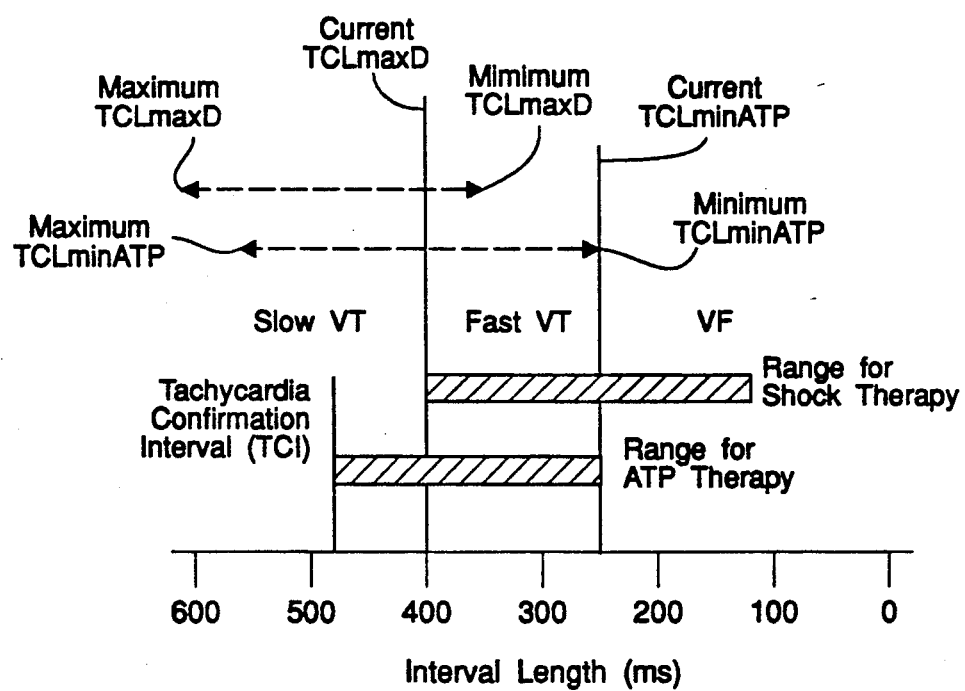
FIG. 12 is a graphic representation of tachycardia classifications as a function of interval length.

Referring to FIG. 12, the sensed cardiac intervals after the detection of an arrhythmia condition are called tachycardia cycle lengths (TCL). TCL governs tachyarrhythmia classification into three types. Slow VT occurs when the tachycardia cycle length is longer than the current TCLmaxD. The pacemaker 17 performs antitachycardia pacing, in deliver therapy block 112 of FIG. 7, only for tachyarrhythmias with a tachycardia cycle length between TCLmaxD and TCI. For cycle lengths longer than TCI, the pacemaker does not perform antitachycardia pacing, as controlled by therapy logic block 111, which directs pacemaker control to return to wait for arrhythmia rate block 100. Fast VT arises when the tachycardia cycle length is longer than the current TCLminATP and shorter than or equal to the current TCLmaxD. In deliver therapy block 112, the pacemaker initiates antitachycardia pacing for cycle lengths within this range, and also uses shock therapy if the abnormal rhythm is not reverted by such therapy. VF occurs when the cycle length is shorter than or equal to the current TCLminATP. For such cycle lengths, the device only employs shock therapy. After performing the selected therapy, pacemaker control returns to wait for arrhythmia rate block 100.

Referring to FIG. 13, there is depicted in illustrative format one embodiment of an antitachycardia pacing algorithm. It is to be understood that the antiarrhythmia pacemaker 17 of the present invention does not limit the antitachycardia therapies to this algorithm but also includes any other algorithms known in the art. A series of M (M=4) pacing trains (a pacing train is a series of pacing spikes controllably delivered in rapid succession ) are delivered. For train 1, the initial A-V delay interval is 10 ms. During a ventricular tachycardia, the atrium and the ventricle are often in dissociation; therefore it is preferable for the dual chamber antitachycardia pacing to begin with a very short atrial to ventricular (A-V) delay interval in order to re-establish association or synchrony as soon as possible between both chambers of the heart. For this reason, the A-V delay is reduced by a predetermined amount. The tachycardia cycle length (TCL) is assumed to be 300 ms. The ventricular to atrial (V-A) delay interval is calculated as a programmable percentage of the TCL for the purpose of adapting to the varying cycle lengths of tachycardias, and has been programmed to be seventy percent of the TCL (300 ms) in this embodiment, thereby establishing the calculated V-A delay interval as 210 ms. In this embodiment, the percentage of the TCL is taken as an average over the four previous sensed intervals, and remains fixed at this value (210 ms) during the course of the therapy. For train 1, N=4, so that at the expiration of each of the 4 V-A delay intervals of 210 ms, an atrial pulse is delivered, and at the expiration of each of the four A-V delay intervals of 10 ms, a pulse is delivered to the ventricle, so that there are a total of N pairs of pulses (or 2N=8 pulses) delivered during train 1.

In train 2 of FIG. 13, the A-V delay interval has been programmed to increment in value from the low initial value of 10 ms in train 1 to the new value of 50 ms. The variation of the A-V delay interval is executed by computer software by standard methods known to those skilled in the art. In the same manner in trains 3 and 4 of FIG. 13, the A-V delay interval increases at the end of trains 2 and 3 to the increased values of 100 ms and 150 ms, respectively. In trains 2, 3, and 4, N=4, as in train 1, thereby delivering N (4) pairs of pacing pulses in each train. In this particular embodiment of the invention, the value of N is equal in all of the trains. However, N is a programmable parameter and may be programmed by the physician to suit the needs of a particular patient. Furthermore, N may have differing values for different trains in alternate embodiments of the invention.

As shown in FIG. 13, the A-V delay interval increments from 10 ms in train 1 to 150 ms in train 4. This parameter is also programmable and is patient dependent. The A-V delay may increment at the end of each train, as in the preferred embodiment. However, the variation in the A-V delay is not necessarily limited to steady increments. It may include any combination of increases, plateaus and decreases in its value. Although it is preferable to include the variations at the end of each train, these may be executed at any time within a train and still fall within the scope of the invention. Preferably, the initial value A-V delay interval is less than or equal to 60 ms.

The V-A delay interval in the preferred embodiment is programmed as a percentage (70%) of the TCL. Although the invention does not limit the V-A delay interval to a particular range, it has been found that the best results occur when it lies within the range of thirty percent to one hundred percent of the TCL. Furthermore, its value is not necessarily fixed during the antitachycardia therapy, but may vary and still remain within the scope of the invention. If it is programmed to vary, the initial value is a percentage of the TCL, for example a percentage of the average cycle length of the last four intervals of the detected tachycardia. For instance, the V-A delay interval may include various combinations of increasing, decreasing, or remaining at a fixed value. Any programmed variations may occur at the end of trains or even within trains, or may even be a function of A-V delay interval variations.

In FIG. 13 the number M of trains selected is 4. This value is also a patient dependent, physician programmable parameter. At the completion of the M trains of antitachycardia pacing, the combined defibrillator pacing device returns to its normal operating mode, including the options of normal dual chamber (DDD) pacing, or defibrillation shocks, if necessary. Furthermore, the device may provide bradycardia support pacing, if required, which may include either single chamber or dual chamber bradycardia support pacing.

It will be apparent from the foregoing description that the present invention makes it possible to provide improved detection and classification of abnormal and harmful cardiac rhythms for the purpose of efficiently and safely performing antitachycardia pacing and defibrillation in an automatic implantable cardiac control system. The improved detection and classification of cardiac rhythms is achieved by analyzing cardiac evoked potential signals, in particular by deriving and evaluating a paced depolarization integral of such signals, to detect changes over time which are characteristic of tachycardia, fibrillation, and asystole conditions. On the basis of the evoked potential analysis, the present invention detects the occurrence of an arrhythmia condition, classifies such condition, and controls the administration and procedure of antitachycardia pacing and defibrillation therapy.

Although the invention has been described with reference to particular embodiments, it is to be understood that such embodiments are merely illustrative of the application of the principles of the invention. Hence numerous modifications may be made therein and other arrangements may be devised without departing from the spirit and scope of the invention.

What is claimed is:

1. An arrhythmia detection and antiarrhythmia pacing device adapted to be implanted in a patient for the reversion of tachycardias, comprising:

means for generating heart stimulation pulses,
   means for measuring an evoked potential of the patient's heart that is responsive to said stimulation pulses,
   means based upon the sensing of an evoked potential for periodically ascertaining the value of a measured arrhythmia detection control parameter,
   means for detecting changes over time in said measured arrhythmia detection control parameter, and
   means responsive to said detecting means for classifying a cardiac rhythm as a pathological tachycardia when said arrhythmia detection control parameter changes in a first predetermined direction and magnitude within a predetermined number of cardiac cycles, and for classifying a cardiac rhythm as a benign physiological tachycardia when said arrhythmia detection control parameter changes in a second predetermined direction and magnitude within a predetermined number of cardiac cycles.

2. An arrhythmia detection and antiarrhythmia pacing device in accordance with claim 1, wherein said arrhythmia detection control parameter is a paced depolarization integral, said pathological tachycardia is characterized generally by an increasing paced depolarization integral, and said benign physiological tachycardia is characterized generally by a paced depolarization integral which decreases or remains unchanged.

3. An arrhythmia detection and antiarrhythmia pacing device in accordance with claim 1, further comprising means responsive to classification of the cardiac rhythm as a pathological tachycardia by said classifying means for controlling said generating means to operate in an antitachycardia pacing mode.

4. An arrhythmia detection and antiarrhythmia pacing device adapted to be implanted in a patient for the reversion of tachycardias, comprising:

means for generating heart stimulation pulses,
   means for measuring an evoked potential of the patient's heart that is responsive to said stimulation pulses,
   means based upon the sensing of an evoked potential for periodically ascertaining the value of a measured arrhythmia detection control parameter,
   means for detecting changes over time in said measured arrhythmia detection control parameter,
   means responsive to said detecting means for classifying a cardiac rhythm as a pathological tachycardia when said arrhythmia detection control parameter changes in a first predetermined direction and magnitude within a predetermined number of cardiac cycles, and for classifying a cardiac rhythm as a benign physiological tachycardia when said arrhythmia detection control parameter changes in a second predetermined direction and magnitude within a predetermined number of cardiac cycles, and
   means responsive to classification of the cardiac rhythm as a pathological tachycardia by said classifying means for controlling said generating means to operate in a dual-chamber antitachycardia pacing mode in which atrial and ventricular pacing pulses are generated and delivered in a series of pulse trains with each train consisting of a series of pacing pulses delivered in rapid succession in an alternating sequence to the ventricle and to the atrium.

5. An arrhythmia detection and antiarrhythmia pacing device adapted to be implanted in a patient for the reversion of tachycardias, comprising:

means for generating heart stimulation pulses,
   means for measuring an evoked potential of the patient's heart that is responsive to said stimulation pulses,
   means based upon the sensing of an evoked potential for periodically ascertaining the value of a measured arrhythmia detection control parameter,
   means for detecting changes over time in said measured arrhythmia detection control parameter,
   means responsive to said detecting means for classifying a cardiac rhythm as a pathological tachycardia when said arrhythmia detection control parameter changes in a first predetermined direction and magnitude within a predetermined number of cardiac cycles, and for classifying a cardiac rhythm as a benign physiological tachycardia when said arrhythmia detection control parameter changes in a second predetermined direction and magnitude within a predetermined number of cardiac cycles,
   means responsive to said detecting means for measuring short-term uniformity of said arrhythmia detection control parameter, and
   means for classifying a cardiac rhythm as fibrillation when said arrhythmia detection control parameter changes in a third predetermined direction and magnitude within a predetermined number of cardiac cycles and said short-term uniformity measurement changes in a fourth predetermined directions and magnitude within a predetermined number of cardiac cycles, 6. An arrhythmia detection and antiarrhythmia pacing device in accordance with claim 5, wherein said arrhythmia detection control parameter is a paced depolarization integral and said fibrillation is characterized in general by a decreasing paced depolarization integral occurring simultaneously with a decreasing short-term uniformity of paced depolarization time samples.

7. An arrhythmia detection and antiarrhythmia pacing device in accordance with claim 5, further comprising:
   means for generating defibrillation shocks; and
   means responsive to the classification of a cardiac rhythm as fibrillation by said classifying means for controlling said defibrillation generating means to generate shocks.

8. An arrhythmia detection and antiarrhythmia pacing device adapted to be implanted in a patient for the reversion of tachycardias, comprising:
   means for generating heart stimulation pulses,
   means for measuring an evoked potential of the patient's heart that is responsive to said stimulation pulses,
   means based upon the sensing of an evoked potential for periodically ascertaining the value of a measured arrhythmia detection control parameter,
   means for detecting changes over time in said measured arrhythmia detection control parameter,
   means for sensing heartbeats,
   means responsive to said heartbeat sensing means for determining a heart rate, and
   means responsive to said detecting means and said heart rate determining means for classifying a cardiac rhythm as a pathological tachycardia when said arrhythmia detection control parameter changes in a first predetermined direction and magnitude within a predetermined number of cardiac cycles and said heart rate is faster than a predetermined tachycardia rate, and for classifying a cardiac rhythm as a benign physiological tachycardia when said arrhythmia detection control parameter changes in a second predetermined direction and magnitude within a predetermined number of cardiac cycles and said heart rate is faster than said tachycardia rate.

9. An arrhythmia detection and antiarrhythmia pacing device in accordance with claim 8, wherein said arrhythmia detection control parameter is a paced depolarization integral, said pathological tachycardia is characterized generally by an increasing paced depolarization integral, and said benign physiological tachycardia is characterized generally by a paced depolarization integral which decreases or remains unchanged.

10. An arrhythmia detection and antiarrhythmia pacing device in accordance with claim 8, further comprising means responsive to classification of the cardiac rhythm as a pathological tachycardia by said classifying means for controlling said generating means to operate in an antitachycardia pacing mode.

11. An arrhythmia detection and antiarrhythmia pacing device adapted to be implanted in a patient for the reversion of tachycardias, comprising:
   means for generating heart stimulation pulses,
   means for measuring an evoked potential of the patient's heart that is responsive to said stimulation pulses,
   means based upon the sensing of an evoked potential for periodically ascertaining the value of a measured arrhythmia detection control parameter,
   means for detecting changes over time in said measured arrhythmia detection control parameter,
   means for sensing heartbeats,
   means responsive to said heartbeat sensing means for determining a heart rate,
   means responsive to said detecting means and said heart rate determining means for classifying a cardiac rhythm as a pathological tachycardia when said arrhythmia detection control parameter changes in a first predetermined direction and magnitude within a predetermined number of cardiac cycles and said heart rate is faster than a predetermined tachycardia rate, and for classifying a cardiac rhythm as a benign physiological tachycardia when said arrhythmia detection control parameter changes in a second predetermined direction and magnitude within a predetermined number of cardiac cycles and said heart rate is faster than said tachycardia rate, and
   means responsive to classification of the cardiac rhythm as a pathological tachycardia by said classifying means for controlling said generating means to operate in an antitachycardia pacing mode,
   wherein said antiarrhythmia pacing device operates in a dual-chamber antitachycardia pacing mode in which atrial and ventricular pacing pulses are generated and delivered in a series of pulse trains with each train consisting of a series of pacing pulses delivered in rapid succession in an alternating sequence to the ventricle and to the atrium.

12. An arrhythmia detection and antiarrhythmia pacing device adapted to be implanted in a patient for the reversion of tachycardias, comprising:
   means for generating heart stimulation pulses,
   means for measuring an evoked potential of the patient's heart that is responsive to said stimulation pulses,
   means based upon the sensing of an evoked potential for periodically ascertaining the value of a measured arrhythmia detection control parameter,
   means for detecting changes over time in said measured arrhythmia detection control parameter,
   means for sensing heartbeats,
   means responsive to said heartbeat sensing means for determining a heart rate,
   means responsive to said detecting means and said heart rate determining means for classifying a cardiac rhythm as a pathological tachycardia when said arrhythmia detection control parameter changes in a first predetermined direction and magnitude within a predetermined number of cardiac cycles and said heart rate is faster than a predetermined tachycardia rate, and for classifying a cardiac rhythm as a benign physiological tachycardia when said arrhythmia detection control parameter changes in a second predetermined direction and magnitude within a predetermined number of cardiac cycles and said heart rate is faster than said tachycardia rate,
   means responsive to said detecting means for measuring short-term uniformity of said arrhythmia detection control parameter, and
   means for classifying a cardiac rhythm as fibrillation when said heart rate is faster than a predetermined fibrillation rate, said arrhythmia detection control parameter changes in a third predetermined direction and magnitude within a predetermined number of cardiac cycles, and said short-term uniformity measurement changes in a fourth predetermined direction and magnitude within a predetermined number of cardiac cycles.

13. An arrhythmia detection and antiarrhythmia pacing device in accordance with claim 12, wherein said arrhythmia control parameter is a paced depolarization integral and said fibrillation is characterized in general by a decreasing paced depolarization integral occurring simultaneously with a decreasing short-term uniformity of paced depolarization time samples.

14. An arrhythmia detection and antiarrhythmia pacing device in accordance with claim 12, further comprising:
means for generating defibrillation shocks and
means responsive to the classification of a cardiac rhythm as fibrillation by said classifying means for controlling said defibrillation generating means to generate shocks.

15. A method of detecting and reverting cardiac arrhythmias of a patient's heart using an anti-arrhythmia pacing device, comprising the steps of:
generating heart stimulation pulses,
measuring an evoked potential of the patient's heart that is responsive to said generated stimulation pulses,
periodically ascertaining the value of a measured arrhythmia detection control parameter which is based upon the sensing of an evoked potential,
detecting changes over time in said measured arrhythmia detection control parameter, and
classifying a cardiac rhythm as a pathological tachycardia when said arrhythmia detection control parameter changes in a first predetermined direction and magnitude within a predetermined number of cardiac cycles, and classifying a cardiac rhythm as a benign physiological tachycardia when said arrhythmia detection control parameter changes in a second predetermined direction and magnitude within a predetermined number of cardiac cycles.

16. A method of detecting and reverting cardiac arrhythmias in accordance with claim 15, wherein said arrhythmia detection control parameter is a paced depolarization integral, said pathological tachycardia is characterized generally by an increasing paced depolarization integral, and said benign physiological tachycardia is characterized generally by a paced depolarization integral which decreases or remains unchanged.

17. A method of detecting and reverting cardiac arrhythmias in accordance with claim 15, further comprising the step of controlling said generating means to operate in an antitachycardia pacing mode in response to classifying a cardiac rhythm as a pathological tachycardia.

18. A method of detecting and reverting cardiac arrhythmias of a patient's heart using an antiarrhythmia pacing device, comprising the steps of:
generating heart stimulation pulses.
measuring an evoked potential of the patient's heart that is responsive to said generated stimulation pulses,
periodically ascertaining the value of a measured arrhythmia detection control parameter which is based upon the sensing of an evoked potential,
detecting changes over time in said measured arrhythmia detection control parameter,
classifying a cardiac rhythm as a pathological tachycardia when said arrhythmia detection control parameter changes in a first predetermined direction and magnitude within a predetermined number of cardiac cycles, and classifying a cardiac rhythm as a benign physiological tachycardia when said arrhythmia detection control parameter changes in a second predetermined direction and magnitude within a predetermined number of cardiac cycles,
controlling said generating means to operate in a dual-chamber antitachycardia pacing mode in response to classifying a cardiac rhythm as a pathological tachycardia, and
generating and delivering a series of pulse trains in the heart's atrium and in the heart's ventricle, with each train consisting of a series of pacing pulses delivered in rapid succession in an alternating sequence to the ventricle and to the atrium.

19. A method of detecting and reverting cardiac arrhythmias of a patient's heart using an antiarrhythmia pacing device, comprising the steps of:
generating heart stimulation pulses,
measuring an evoked potential of the patient's heart that is responsive to said generated stimulation pulses,
periodically ascertaining the value of a measured arrhythmia detection control parameter which is based upon the sensing of an evoked potential,
detecting changes over time in said measured arrhythmia detection control parameter,
classifying a cardiac rhythm as a pathological tachycardia when said arrhythmia detection control parameter changes in a first predetermined direction and magnitude within a predetermined number of cardiac cycles, and classifying a cardiac rhythm as a benign physiological tachycardia when said arrhythmia detection control parameter changes in a second predetermined direction and magnitude within a predetermined number of cardiac cycles,
measuring short-term uniformity of said arrhythmia detection control parameter, and
classifying a cardiac rhythm as fibrillation when said arrhythmia detection control parameter changes in a third predetermined direction and magnitude within a predetermined number of cardiac cycles and said short-term uniformity measurement changes in a fourth predetermined direction and magnitude within a predetermined number of cardiac cycles.

20. A method of detecting and reverting cardiac arrhythmias in accordance with claim 19, wherein said arrhythmia control parameter is a paced depolarization integral and said fibrillation is characterized in general by a decreasing paced depolarization integral occurring simultaneously with a decreasing short-term uniformity of paced depolarization time samples.

21. A method of detecting and reverting cardiac arrhythmias in accordance with claim 19, further comprising the steps of:
generating defibrillation shocks; and
controlling said defibrillation generating step to generate shocks in response to classification of a cardiac rhythm as fibrillation in said classifying step.

22. A method of detecting and reverting cardiac arrhythmias of a patient's heart using an anti-arrhythmia pacing device, comprising the steps of:
generating heart stimulation pulses,
measuring an evoked potential of the patient's heart that is responsive to said stimulation pulses,
periodically ascertaining the value of a measured arrhythmia detection control parameter which is based upon the sensing of an evoked potential,
detecting changes over time in said measured arrhythmia detection control parameter,
sensing heartbeats,
timing the interval between sensed heartbeats to determine a heart rate, and classifying a cardiac rhythm as a pathological tachycardia when said arrhythmia detection control parameter changes in a first predetermined direction and magnitude within a predetermined number of cardiac cycles and said heart rate is faster than a predetermined tachycardia rate, and classifying a cardiac rhythm as a benign physiological tachycardia when said arrhythmia detection control parameter changes in a second predetermined direction and magnitude within a predetermined number of cardiac cycles and said heart rate is faster than said tachycardia rate.

23. A method of detecting and reverting cardiac arrhythmias in accordance with claim 22, wherein said arrhythmia detection control parameter is a paced depolarization integral, said pathological tachycardia is characterized generally by an increasing paced depolarization integral, and said benign physiological tachycardia is characterized generally by a paced depolarization integral which decreases or remains unchanged.

24. A method of detecting and reverting cardiac arrhythmias in accordance with claim 22, further comprising the step of controlling said generating means to operating in an antitachycardia pacing mode in response to classifying a cardiac rhythm as a pathological tachycardia.

25. A method of detecting and reverting cardiac arrhythmias of a patient's heart using an antiarrhythmia pacing device, comprising the steps of:
generating heart stimulation pulses,
measuring an evoked potential of the patient's heart that is responsive to said stimulate pulses,
periodically ascertaining the value of a measured arrhythmia detection control parameter which is based upon the sensing of an evoked potential,
detecting changes over time in said measured arrhythmia detection control parameter,
sensing heartbeats,
timing the interval between sensed heartbeats to determine a heart rate,
classifying a cardiac rhythm as a pathological tachycardia when said arrhythmia detection control parameter changes in a first predetermined direction and magnitude within a predetermined number of cardiac cycles and said heart rate is faster than a predetermined tachycardia rate, and classifying a cardiac rhythm as a benign physiological tachycardia when said arrhythmia detection control parameter changes in a second predetermined direction and magnitude within a predetermined number of cardiac cycles and said heart rate is faster than said tachycardia rate,
controlling said generating means to operate in a dual-chamber antitachycardia pacing mode in response to classifying a cardiac rhythm as a pathological tachycardia, and
generating and delivering a series of pulse trains in the heart's atrium and in the heart's ventricle, with each train consisting of a series of pacing pulses delivered in rapid succession in an alternating sequence to the ventricle and to the atrium.

26. A method of detecting and reverting cardiac arrhythmias of a patient's heart using an antiarrhythmia pacing device, comprising the steps of:
generating heart stimulation pulses,
measuring an evoked potential of the patient's heart that is responsive to said stimulation pulses,
periodically ascertaining the value of a measured arrhythmia detection control parameter which is based upon the sensing of an evoked potential,
detecting changes over time in said measured arrhythmia detection control parameter,
sensing heartbeats,
timing the interval between sensed heartbeats to determine a heart rate,
classifying a cardiac rhythm as a pathological tachycardia when said arrhythmia detection control parameter changes in a first predetermined direction and magnitude within a predetermined number of cardiac cycles and said heart rate is faster than a predetermined tachycardia rate, and classifying a cardiac rhythm as a benign physiological tachycardia when said arrhythmia detection control parameter changes in a second predetermined direction and magnitude within a predetermined number of cardiac cycles and said heart rate is faster than said tachycardia rate,
measuring short-term uniformity of said arrhythmia detection control parameter, and
classifying a cardiac rhythm as fibrillation when said heart rate is faster than a predetermined fibrillation rate, said arrhythmia detection control parameter changes in a third predetermined direction and magnitude within a predetermined number of cardiac cycles, and said short-term uniformity measurement changes in a fourth predetermined direction and magnitude within a predetermined number of cardiac cycles.

27. A method of detecting and reverting cardiac arrhythmias in accordance with claim 26, wherein said arrhythmia detection control parameter is a paced depolarization integral and said fibrillation is characterized in general by a decreasing paced depolarization integral occurring simultaneously with a decreasing short-term uniformity of paced depolarization time samples.

28. A method of detecting and reverting cardiac arrhythmias in accordance with claim 26, further comprising the steps of:
generating defibrillation shocks; and
controlling said defibrillation generating step to generate shocks in response to classification of a cardiac rhythm as fibrillation in said classifying step.

29. An arrhythmia detection and antiarrhythmia pacing device adapted to be implanted in a patient for the reversion of tachycardias, comprising:
means for generating heart stimulation pulses,
means for measuring an evoked potential of the patient's heart that is responsive to said stimulation pulses,
means based upon the sensing of an evoked potential for periodically ascertaining the value of a measured arrhythmia detection control parameter,
means for detecting changes over time in said measured arrhythmia detection control parameter,
means for sensing heartbeats,
means responsive to said heartbeat sensing means for determining a heart rate, and
means responsive to said detecting means and said heart rate determining means for classifying a cardiac rhythm as asystole when said heart rate is slower than a predetermined bradycardia rate and said arrhythmia detection control parameter remains essentially unchanged within a predetermined number of cardiac cycles, and for classifying a cardiac rhythm as fibrillation when said heart rate is slower than a predetermined bradycardia rate and said arrhythmia detection control parameter changes in a predetermined direction and magnitude within a predetermined number of cardiac cycles.

30. An arrhythmia detection and antiarrhythmia pacing device in accordance with claim 29, wherein said arrhythmia control parameter is a paced depolarization integral and said asystole is characterized in general by an essentially unchanging paced depolarization integral and said fibrillation is characterized in general by a reduced paced depolarization integral.

31. A method of detecting and reverting cardiac arrhythmias of a patient's heart using an antiarrhythmia pacing device, comprising the steps of:
generating heart stimulation pulses,
measuring an evoked potential of the patient's heart that is responsive to said stimulation pulses,
periodically ascertaining the value of a measured arrhythmia detection control parameter which is based upon the sensing of an evoked potential,
detecting changes over time in said measured arrhythmia detection control parameter,
sensing heartbeats,
timing the interval between sensed heartbeats to determine a heart rate, and
classifying a cardiac rhythm as asystole when said heart rate is slower than a predetermined bradycardia rate and said arrhythmia detection control parameter remains essentially unchanged within a predetermined number of cardiac cycles, and classifying a cardiac rhythm as fibrillation when said heart rate is slower than a predetermined bradycardia rate and said arrhythmia detection control parameter changes in a predetermined direction and magnitude within a predetermined number of cardiac cycles.

* * * * *